United States Patent [19]

Rosenberg

[11] Patent Number: 5,483,970

[45] Date of Patent: * Jan. 16, 1996

[54] APPARATUS AND METHODS FOR THE DIAGNOSIS OF LABOR

[75] Inventor: Ethan Rosenberg, Monsey, N.Y.

[73] Assignee: Hygeia Biomedical Research Inc., Monsey, N.Y.

[ * ] Notice: The portion of the term of this patent subsequent to Apr. 12, 2011, has been disclaimed.

[21] Appl. No.: 193,284

[22] Filed: Feb. 8, 1994

Related U.S. Application Data

[63] Continuation of Ser. No. 988,433, Dec. 9, 1992, Pat. No. 5,301,680.

[51] Int. Cl.$^6$ ................................................. A61B 5/0488
[52] U.S. Cl. .......................... 128/733; 128/775; 128/778; 128/903
[58] Field of Search ................................... 128/733, 775, 128/778, 903–904

[56] References Cited

U.S. PATENT DOCUMENTS

| | | |
|---|---|---|
| 4,256,118 | 3/1981 | Nagel . |
| 4,719,925 | 1/1988 | Parsons . |
| 4,967,761 | 11/1990 | Nathanielsz . |
| 5,042,503 | 8/1991 | Torok et al. . |
| 5,301,680 | 4/1994 | Rosenberg ............................ 128/733 |

FOREIGN PATENT DOCUMENTS

| | | |
|---|---|---|
| 3729760 | 3/1989 | Germany . |
| 0306915 | 3/1989 | Germany . |

OTHER PUBLICATIONS

Wolfs et al., "Electromyographic Observations on the Human Uterus during Labour", Acta Obstet. Gynecol. Scand. S7ppl. 90, (1979), pp. 6–61.

Pronin; "Instrument for Measuring the Contractile Activity of the Uterus"; *Biomedical Engineering;* vol. 7, No. 4; May 1974; pp. 212–215.

Planes et al., "External recording and processing of fast electrical activity of the uterus in human parturition", Medical & Biological Engineering & Computing, Nov. 1984, pp. 585–591.

Dill et al., "The Electrical Potentials of the Human Uterus in Labor", Amer. J. Obstet. Gynecol., vol. 52, 735 (1946), pp. 735–745.

Steer et al., "Electrical Activity of the Human Uterus in Labor", Amer. J. Obstet. Gynecol., vol. 59, 25 (1950), pp. 25–40.

*Primary Examiner*—Angela D. Sykes
*Attorney, Agent, or Firm*—Perman & Green

[57] ABSTRACT

Disclosed are methods and apparatus for the electromyographic detection of electrical fields inherent in muscular activity, for the diagnosis of labor in a pregnant mammal. The apparatus includes a system (10) for determining a periodicity, and for measuring a magnitude and a direction of movement, of the electrical signal in an abdominal region, and for processing the signal to indicate normal and abnormal labor conditions, the onset of true labor, and the extent of cervical dilation. A Labor Onset processor (16e) determines the onset of true labor. A Vector Determination processor (16b) determines a uterine contraction vector having a propagation rate component and a direction component, relative to a plurality of measurement electrodes. The positions of the measurement electrodes are referenced to a coordinate system and are specified to the system through a data entry device (20). A display (18a, 18b) provides a visual or audible indication of labor diagnostic information, the diagnostic information being expressed in a number of formats. The invention also provides for remotely monitoring a pregnant mammal through the use of a communications link (32).

21 Claims, 18 Drawing Sheets

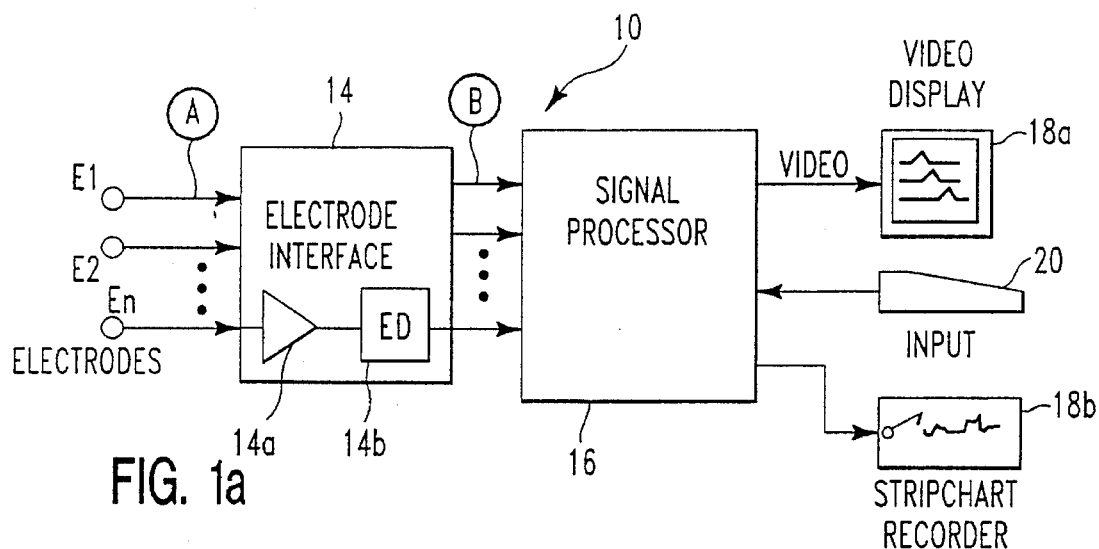
FIG. 1a
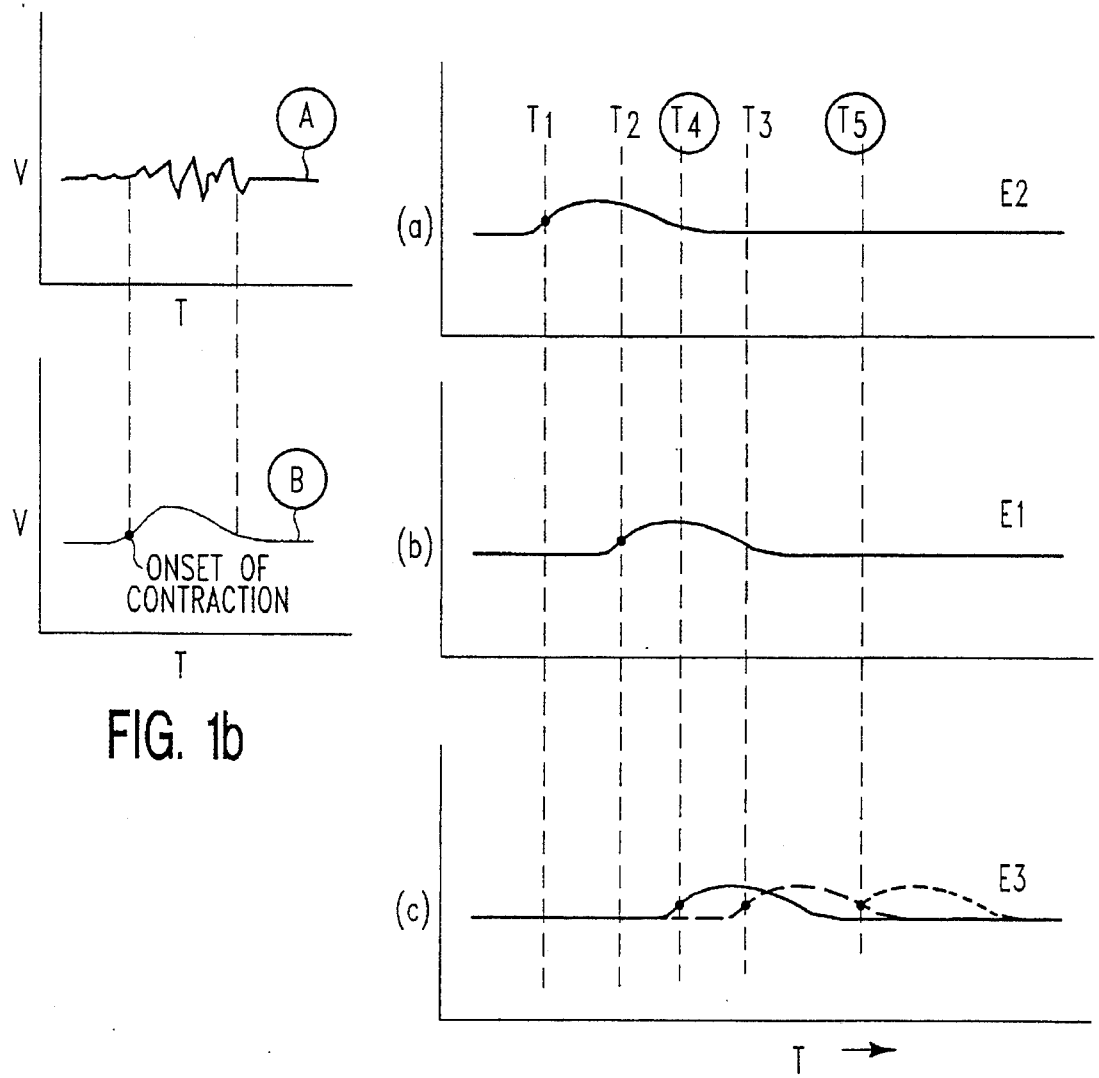
FIG. 1b
DISPLAY 1
FIG. 1c

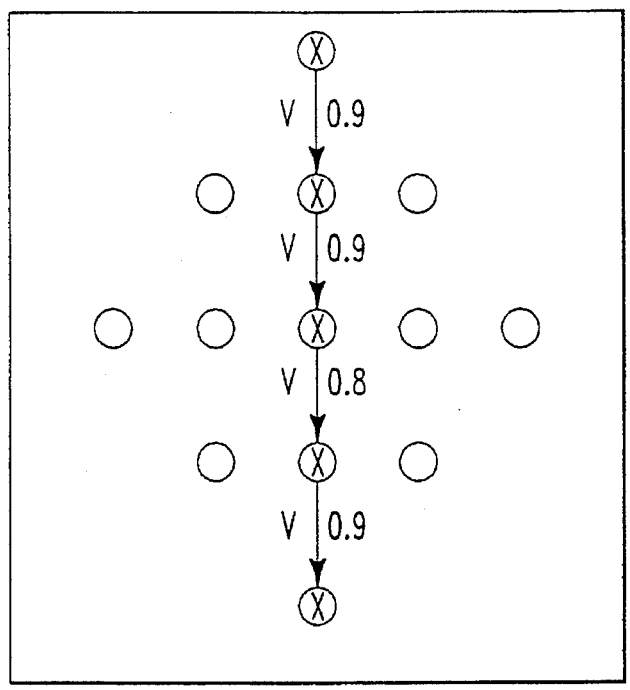
FIG. 1e DISPLAY 2
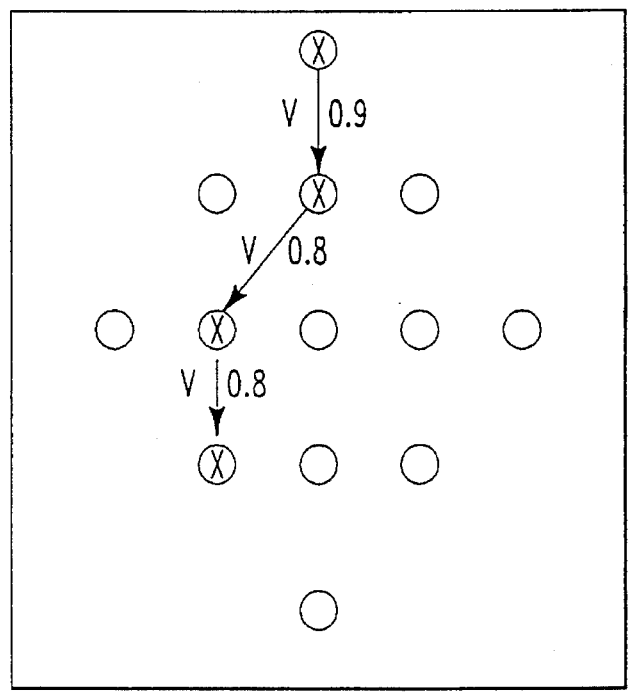
FIG. 1f DISPLAY 2

APPARATUS AND METHODS FOR THE DIAGNOSIS OF LABOR

This is a continuation of application(s) Ser. No. 07/988,433 filed on Dec. 9, 1992, now U.S. Pat. No. 5,301,680 and which designated the U.S.

FIELD OF THE INVENTION

This invention relates generally to medical and veterinary instrumentation and, in particular, to medical and veterinary instrumentation for use in monitoring labor.

BACKGROUND OF THE INVENTION

A well known method of monitoring the progress of labor in a pregnant woman utilizes the hands of a medical practitioner to palpate the abdomen to assess both the strength of a uterine contraction, and the progression of the contraction down the uterus, it being known that a "normal" uterine contraction during true labor originates at the fundus of the uterus and propagates towards the cervix. Of equal importance is the patient's own evaluation as to the progress of her labor. In addition, the extent of cervical dilation is estimated via an intra-vaginal examination. However, the accuracy of these manual methods of monitoring the progress of labor are directly related to the skill of the examiner. Furthermore, these conventional techniques are non-continuous, uncomfortable for the patient, and, for any invasive procedure, pose a risk of infection.

With the advent of medical electronics, instrumentation has taken over many of these functions. Instrumentation can be automated, operated continuously, will not tire, and can, thereby, relieve the practitioner. However, the use of conventional instrumentation presents several problems.

For example, the present technology employed for measuring uterine contractions does not yield data of significant diagnostic value. The conventional contraction monitors that are known to the inventor are primarily used to detect fetal distress, by correlating the data from a uterine contraction monitor with the fetal heart rate. However, since these monitors typically obtain data at only one location on the uterus, they do not yield information as to the progression of the uterine contraction. As a result, conventional monitors yield no data as to the status of the uterine muscle itself.

There are two types of contraction monitors in general use today: external monitors and internal monitors. The drawbacks of both are described below.

Typically, the external monitor consists of a strain gauge attached with a strap to the patient's abdomen. The gauge generates qualitative data on the strength of the uterine contractions. However, absolute pressure cannot be measured by this method, since it does not directly measure the internal pressure of the uterus.

Also, external monitors are uncomfortable for the patient. If the patient does not lie perfectly still (which is often difficult for a woman in labor), the data is flawed by artifacts. Patients must also lie flat on their backs, thereby allowing the weight of the uterus to possibly compress the ascending vena cava (the vein which returns the blood to the heart from the lower body), thereby compromising both the maternal and fetal circulation, with possible deleterious results for both.

The internal monitor measures the pressure exerted by the uterus on an intra-uterine pressure transducer. This method can yield semi-quantitative data regarding the contractions in terms of pressure.

However, this method can only be used if the cervix is dilated and the membranes have ruptured. As a consequence, it can only be used in a hospital setting, with patients in active labor. This method carries with it the risk of infection, since the transducer must pass through the bacterial flora of the vagina. These organisms may then be introduced into the uterus, and there can infect both mother and fetus.

In addition, since the membranes are not intact, a closed vessel does not exist, and Pascal's Law, which states that the pressure measured at one location in a closed vessel is the same at all points in that vessel, does not apply. As a result, the intra-uterine catheter measures different pressures, depending upon where it is located. Thus, the pressure measured by the intra-uterine catheter can be considered as semi-quantitative at best. Furthermore, this method cannot be used at all in the case of placenta previa, wherein the placenta lies across the opening of the cervix.

Also, at the present time, there is no known instrumental method, which is not invasive in nature, for continuously measuring the extent of cervical dilation. That is, some type of device must be introduced intravaginally to obtain the measurement, with the attendant drawbacks referred to above.

Recognizing the above described drawbacks, medical investigators have sought a method which would yield data of greater value. Early attempts to record the electrical activity of the smooth uterine muscle have been recorded in the medical literature.

By example, L. V. Dill et al. describe, in an article entitled "The Electrical Potentials of the Human Uterus in Labor", Amer. J. Obstet. Gynecol., Vol. 52, 735 (1946), the observation that the contraction of the uterine muscle during labor is accompanied by changes in potential of low frequency and voltage. C. M. Steer et al. describe, in an article entitled "Electrical Activity of the Human Uterus in Labor" Amer J. Obstet. Gynecol., Vol. 59, 25 (1950), various observations of electrical activity recorded at points on the abdominal wall. Early labor is said to be associated with electrical activity at one of three usual points on the abdominal wall. As labor advances, more leads become active. These authors also note evidence suggesting a propagation of electrical activity during early normal labor.

Using internal electrodes to collect the signal, an extensive set of experiments was performed in humans by Wolfs et al. in 1979. Results of these experiments are reported in "Electromyographic Observations on the Human Uterus during Labour", Acta Obstet. Gynecol. Scand. Suppl. 90, (1979).

Because of the risks involved, and the availability of suitable animal models, such as sheep, the use of internal electrodes in human subjects has not been actively pursued. Internal electrodes are still used extensively in sheep, primarily to measure the frequency and duration of electrical activity.

In U.S. Pat. No. 4,967,761 Nathanielsz teaches the use of internal electrodes to differentiate true from false labor by measuring and analyzing the frequency of the electrical activity of the uterus.

In U.S. Pat. No. 4,256,118 Nagel teaches the use of external electrodes to measure both the electrical activity of the uterus and the fetal heart rate. Nagel describes a range of frequencies of 150 Hz to 250 Hz for the electrical activity of the uterus. It is noted, however, that this range of frequencies is typically associated with intra-uterine measurements, whereas frequencies obtained with external electrodes are primarily in the range of 0.05 Hz to 2 Hz.

In an article entitled "External Recording and Processing of Fast Electrical Activity of the Uterus in Human Parturition" Med & Bio Eng & Comput, 22, 585–91 (1984), J. Planes et al. describe the use of external electrodes to monitor the electrical activity of the uterine muscle during labor. Using an autoregression analysis, Planes et al. characterize a contraction by six parameters. Planes et al. estimate a propagation velocity of the contraction, but do not obtain any information concerning the direction of propagation, stress on the uterine musculature, or cervical dilation. Also, Planes et al. do not suggest the use of this information for diagnostic purposes.

For example, abnormal stress on any part of the uterine muscle is known to produce a marked change in the rate of progression of the electrical activity down the uterus. Abnormal stress may be due to the presence of scar tissue, such as that resulting from a previously performed cesarean section. The detection and characterization of a change in the rate of progression would thus be a diagnostic determination of great value to the practitioner.

It is thus one object of this invention to provide a method, and apparatus for accomplishing the method, whereby true labor is distinguished from false labor and other pathological conditions, by measuring the rate and direction of movement of the electrical activity of the uterine muscle.

It is a further object of this invention to provide a method, and apparatus for accomplishing the method, for diagnosing the presence of undue stress on any part of the uterine muscle by detecting abrupt changes in the rate of movement of the electrical activity of the uterine muscle.

It is a further object of this invention to provide a method, and apparatus for accomplishing the method, for diagnosing the onset of true labor by determining the direction of movement and periodicity of the electrical activity of the uterine muscle.

It is another object of this invention to provide a method, and apparatus for accomplishing the method, for utilizing a direct current offset of an electrical signal to measure the extent of cervical dilation.

A still further object of the invention provides instrumentation for remotely monitoring a pregnant mammal to aid in diagnosing: (a) true labor from false labor and other pathological conditions, (b) the presence of undue stress on any part of the uterine muscle, (c) the onset of true labor, and/or (d) the extent of cervical dilation.

SUMMARY OF THE INVENTION

The foregoing and other problems are overcome and the objects of the invention are realized by methods and apparatus utilizing an electromyographic detection of electrical fields inherent in muscular activity for the diagnosis of labor. The apparatus includes a system for measuring the magnitude and direction of movement of an electrical signal in the abdominal region, and for processing the signal to indicate normal and abnormal labor conditions, the onset of true labor, and also the extent of cervical dilation.

The system senses electrical activity indicative of a smooth muscle contraction, such as a uterine contraction, and correlates the electrical activity with a specific external electrode. Using predetermined coordinates of the electrode, and any or all other electrode(s) sensing the same contraction, the system of the invention determines and displays a contraction propagation vector having a velocity and a direction.

More specifically, an envelope of the electrical activity of the uterine muscle is determined by an envelope detector, and is displayed on a computer monitor, chart recorder, or other appropriate display apparatus. The envelope is processed so as to be related to an intra-uterine pressure curve. As a result, the strength of a uterine contraction is measured at a plurality of points.

This invention teaches (a) the detection and display of the envelope of the detected electrical activity, (b) the calculation of the rate and direction of movement of the electrical activity, and (c) the display of the results of the calculation so as to provide diagnostic information regarding a uterine contraction. Further in accordance with the teaching of the invention, (d) a warning indication is displayed if the results of the above calculation indicate an abnormal state.

This invention furthermore teaches (e) the detection of electrical activity indicative of the onset of true labor and (f) the display of an indication when the onset of labor is detected.

This invention furthermore teaches (g) the detection of a direct current offset of the electrical activity of the uterine muscle, (h) the correlation of the direct current offset with the degree of cervical dilation, and (i) the display of a change in cervical dilation as a function of time.

This invention furthermore teaches the remote monitoring of a pregnant mammal, in combination with methods and apparatus for enabling a practitioner to remotely make a diagnosis so as to distinguish (a) true labor from false labor and other pathological conditions, (b) to determine the presence of undue stress on any part of the uterine muscle, (c) to detect the onset of true labor, and/or (d) to determine the extent of cervical dilation.

BRIEF DESCRIPTION OF THE DRAWINGS

The above set forth and other features of the invention are made more apparent in the ensuing Detailed Description of the Invention when read in conjunction with the attached Drawings, wherein:

FIG. 1a is a block diagram of a labor diagnostic system that is constructed and operated in accordance with the invention;

FIG. 1b illustrates typical waveforms obtained at the nodes A and B of FIG. 1a;

FIG. 1c illustrates a first display (DISPLAY1) of the progression of a uterine contraction as detected by three electrodes that are coupled to the system of FIG. 1a;

FIGS. 1d(a) and (b) illustrate a second display (DISPLAY2) of a possible location of the electrodes and a progression of a uterine contraction as detected by the electrodes that are coupled to the system of FIG. 1a;

FIGS. 1e and 1f illustrate further examples of the DISPLAY2 showing a possible location of the electrodes and a progression of a uterine contraction;

FIG. 10 depicts the relationship of FIGS. 10A and 10B to one another, wherein FIGS. 10A and 10B together depict a logic diagram of a method for operating a Vector Determination processor of FIGS. 2 and 3 wherein FIGS. 10A and 10B are hereinafter collectively referred to as FIG. 10;

FIG. 14 depicts the relationship of FIGS. 14a and 14b to one another, wherein FIGS. 14a and 14b together depict a logic diagram of a method for operating a Labor Onset processor of FIG. 3a.

FIGS. 14a and 14b are hereinafter collectively referred to as FIG. 14.

DETAILED DESCRIPTION OF THE INVENTION

Figure 1D:
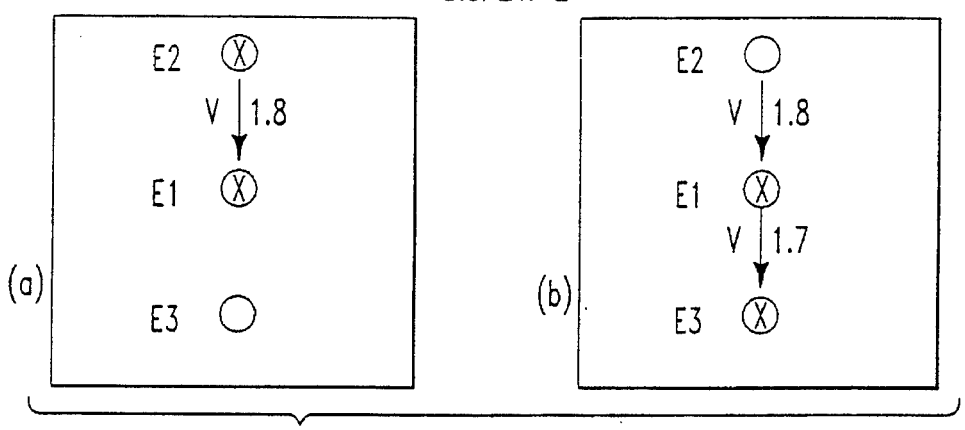

As employed herein, the term "pregnant mammal" is not intended to be limited to only a pregnant human female, in that the methods and apparatus of this invention may be utilized by both medical and veterinary practitioners.

Also as employed herein, the term "diagnostic information" is intended to refer to data and/or signals (audible and/or visible) emanating from the apparatus of the invention, the data and/or signals being the result of the processing by the apparatus, in accordance with the methods of the invention, of the voltages detected by suitable transducers, such as electrodes, that are attached to a pregnant mammal. These voltages may be detected and processed in close proximity to the pregnant mammal, or may be transmitted over a suitable telemetry or communications link and processed remotely from the pregnant mammal. Furthermore, the data and/or signals are presented to a practitioner in such a manner so as to aid the practitioner in distinguishing true labor from false labor and other pathological conditions. The data and/or signals are also presented to the practitioner in such a manner so as to aid the practitioner in determining the presence of undue stress on any part of the uterine muscle, the onset of true labor, and the extent of cervical dilation.

FIG. 1a is a block diagram of a Labor Diagnostic System (LDS) 10 that is constructed and operated in accordance with the invention. The LDS 10 includes an electrode interface 14 having inputs for receiving signals from a plurality of electrodes (E1–E(n)). The electrode interface 14 includes a plurality of differential amplifiers 14a (only one of which is shown in FIG. 1a), each having an output feeding an associated Envelope Detector (ED) 14b. FIG. 1b illustrates typical waveforms obtained at the nodes A and B of FIG. 1a, and shows the operation of the Envelope Detector 14b in smoothing the amplified electrode signal.

The outputs of the Envelope Detectors 14b are coupled to inputs of a Signal Processor 16. As seen in FIGS. 2, 3, 3a, and 4, the Signal Processor 16 includes logic and/or analog circuitry that provides an Activity Detector processor 16a, a Vector Determination processor 16b, a Rate of Change processor 16c and, optionally, a DC Offset processor 16d or a Labor Onset processor 16e. The operation of processors 16a–16e is described in detail below.

Coupled to Signal Processor 16 are various input and output (I/O) devices. These (I/O) devices may include a video display monitor 18a, preferably having graphical capability, and a data entry device such as a keyboard 20. A strip chart recorder 18b may also be provided to supplement the display capabilities of the LDS 10 and to provide a permanent record of labor-related data that is derived from a patient to which the electrodes are affixed during use of the LDS 10.

It should be realized that the embodiment of FIG. 1a is exemplary, and that the functionality of the LDS 10 may be embodied within a large number of suitable hardware and/or software systems. By example, each of the processors 16a–16e may be a separate microprocessor that executes a program for implementing the logic flow diagrams shown in FIGS. 9, 10, 11, 12, and 14, respectively. Additionally, the logic flow diagrams shown in FIGS. 8, 8a, and 8b may be implemented by separate microprocessors. Alternately, a single processing device, such as one embodied within a personal computer, may execute all of these functions. Furthermore, the electrode interface 14 may be provided as a unit separate from the signal processor 16, or may be incorporated within the signal processor 16 as a plug-in circuit board having appropriate electrode interface circuitry or by some other method known to those skilled in the art. It should further be noted that many functions may be performed by analog circuitry, or by a suitably programmed digital signal processor (DSP) device. By example, the Envelope Detector 14b may be embodied within a low pass filter comprised of analog circuit components, or may be embodied in a software routine, executed by a digital signal processor, that receives a digitized representation of the waveform appearing at the output of the amplifiers 14a. It should thus be apparent that the teaching of this invention is not to be construed to be limited to any one specific assemblage of hardware and/or software components.

Figure 2:
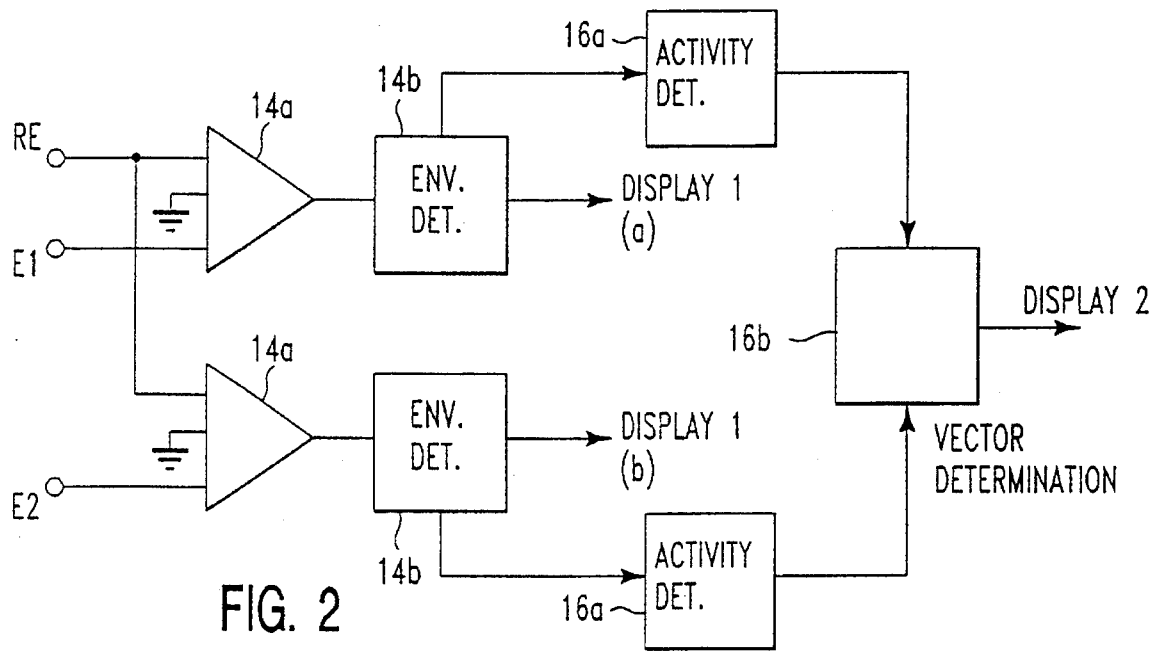
FIG. 2 is a block circuit diagram of a first embodiment of the apparatus according to the invention in which circuitry is provided to detect and display uterine activity at a plurality of points, and in which circuitry is provided to determine and display the rate and direction of movement of such activity.

Referring now to FIG. 2 there is shown a block diagram of a first embodiment of apparatus in which circuitry is provided to detect and display uterine activity at a plurality of points, and in which circuitry is provided to determine and display the rate and direction of movement of such activity. A plurality of the electrodes, which may be EKG (or equivalent) electrodes, are attached to a patient whose uterine contraction activity is to be measured.

Figure 7A:
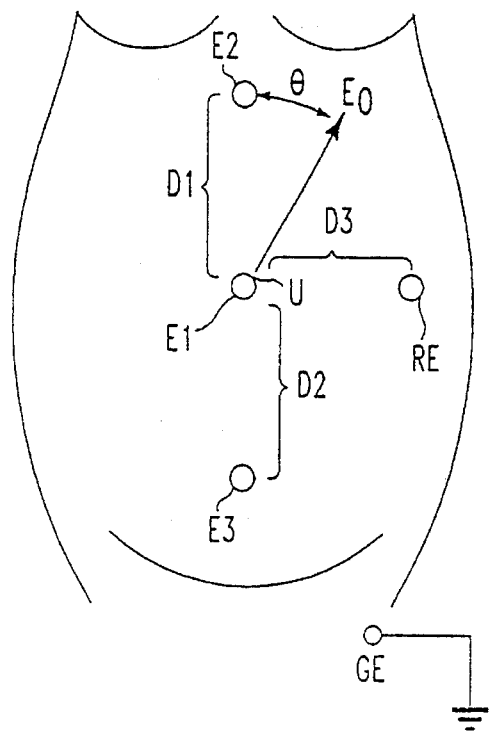
FIG. 7a is a diagram of one possible electrode placement configuration and of a possible coordinate system associated with the electrode placement.

One suitable number of electrodes is four, two to serve as measuring electrodes, one as a common reference electrode (RE), and one as a common ground electrode (GE). For the case where three measuring electrodes are employed, a preferred electrode placement is shown in FIG. 7a, where E1, E2, and E3 are the measuring electrodes, RE is the reference electrode, and GE is the ground electrode. U is the patient's umbilicus, which is employed as a reference point. The first electrode, E1, is positioned in the near vicinity of the umbilicus. The second electrode, E2, is positioned on a line extending from the umbilicus upward to the xiphoid at a first distance (D1) from E1. The third electrode, E3, is positioned on the downward extension of the above mentioned line at a distance D2 from E1. The reference electrode, RE, is positioned on a line passing through the umbilicus, perpendicular to the above mentioned line, at a distance D3 from E1. The ground electrode, GE, is preferably positioned on the upper thigh. By example, D1, D2 and D3 are each approximately 10 centimeters.

Figure 7B:
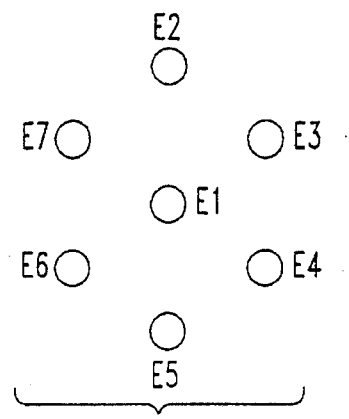
FIG. 7b is a diagram of a second possible electrode placement configuration.

For the case where seven measuring electrodes are employed, a preferred electrode placement is shown in FIG. 7b, where E1–E7 are the measuring electrodes.

As seen in FIG. 7a, which shows the coordinates of the generalized electrode, $E_0$, the electrodes may be referenced to a polar coordinate system, with a distance, D, and an angle, θ, using the umbilicus as the origin. The distance, D, is measured from the umbilicus. The angle, θ, is measured in a clockwise direction from the line passing through the umbilicus and the xiphoid. The electrodes, however, may be referenced to any two dimensional coordinate system such as, for example, an x,y coordinate system.

Prior to attaching the electrodes to the patient, the practitioner may choose to utilize one of a number of standard electrode configurations which have been programmed into the LDS 10, or, if a user preferred electrode configuration is frequently employed, to generate the data for the frequently used electrode configuration. In the latter case, following the logic flow diagram shown in FIG. 8b, at Block A, an operator inputs a designator, for example, a number, to identify a particular user preferred coordinate system. At Block B an operator inputs an electrode number, which is accepted and stored by the Signal Processor 16. Blocks C and D are then executed to input, accept, and store the Distance, D, and the Angle, e, respectively. At Block E a determination is made if a further electrode is to be entered. If NO, control passes to Block F where the electrode entry routine is terminated. If YES at Block E, control returns to Block B to enter the next electrode number.

After the standard electrode configuration has been entered, the Signal Processor 16 performs operations upon the coordinates in accordance with Blocks A through F of FIG. 8a, as described in detail below.

Figure 7D:
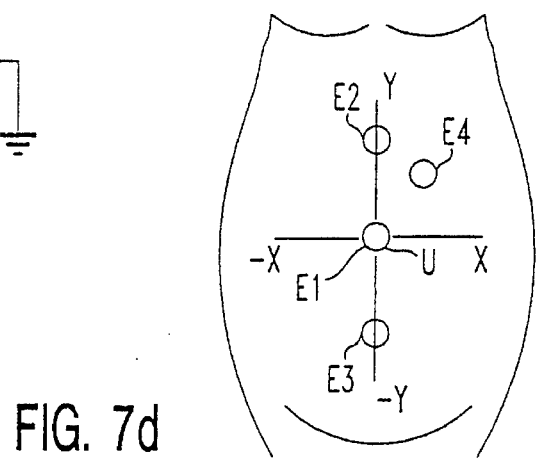
FIG. 7d illustrates a second exemplary electrode placement coordinate system, specifically a Cartesian coordinate system.
Figure 8:
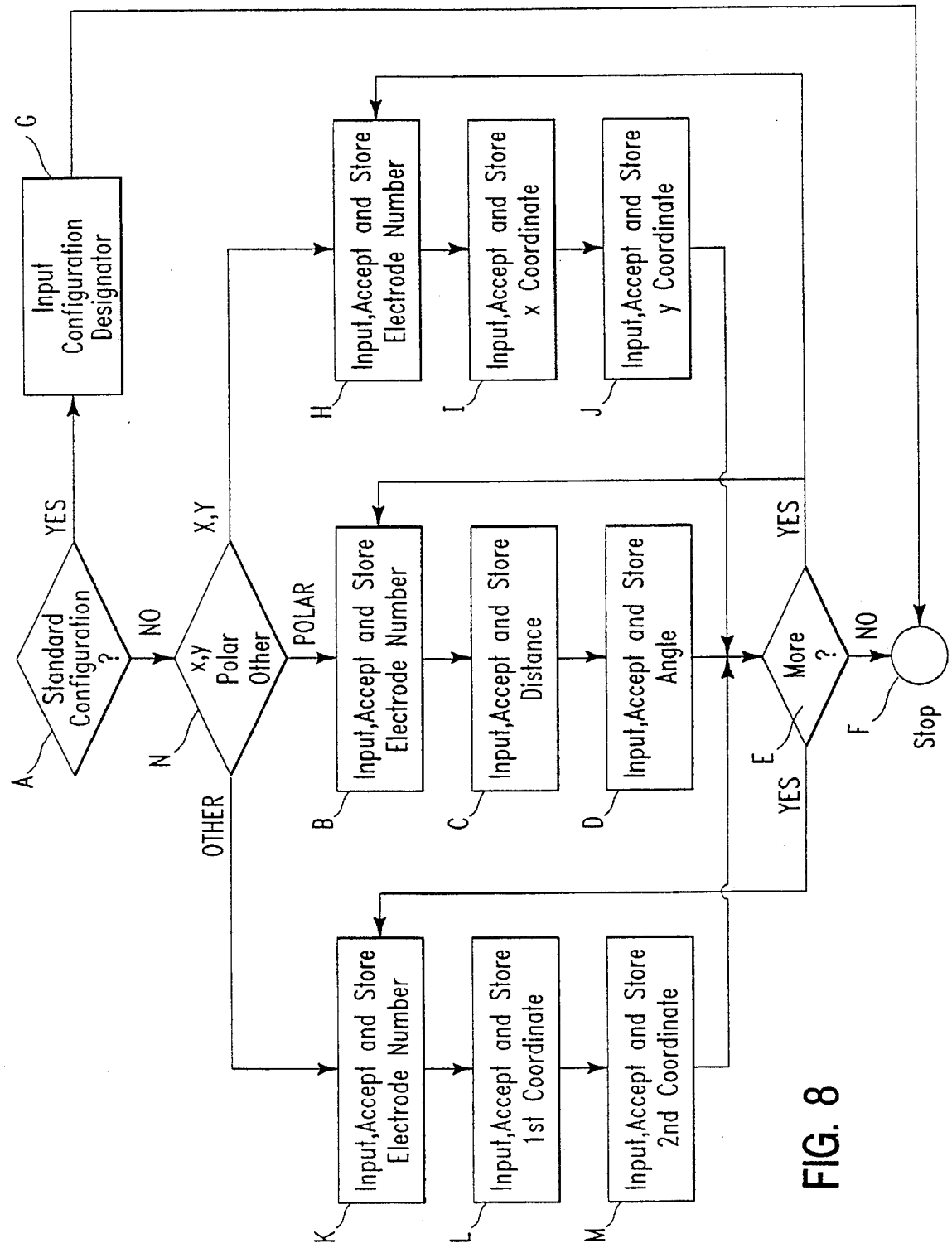
FIG. 8 is a logic diagram of a method of inputting and accepting the coordinates of the electrodes.
Figure 8B:
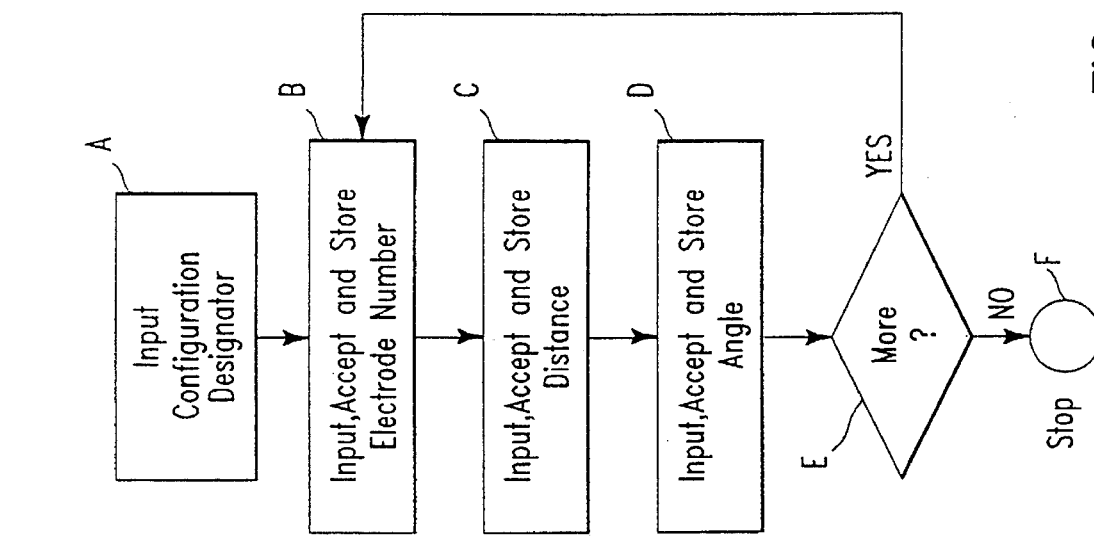
FIG. 8b is a logic diagram of a method of inputting and accepting the coordinates of the electrodes used in a standard electrode configuration.

In accordance with a further method, after positioning and attaching the electrodes the practitioner employs the keyboard 20 of FIG. 1a to input to the Signal Processor 16 the electrode identifiers, the distances D, and the corresponding angles θ, in accordance with the logic diagram of FIG. 8. At Block A, an operator inputs a value indicating if the electrode configuration is one of the standard configurations. If YES at Block A, an operator enters a value at Block G indicating which one of the standard configurations is being used. The electrode coordinates of the standard electrode configuration, along with the results of the operations of Blocks A through F of FIG. 8a, are then retrieved from storage and referenced in any further operations performed by the Signal Processor 16. Control then passes to Block F where the electrode entry routine is terminated. If NO at Block A, at Block N the operator inputs a value indicating the type of coordinate system being used. If a polar coordinate system is being used, at Block B an operator inputs an electrode number, which is accepted and stored by the Signal Processor 16. Blocks C and D are then executed to input, accept, and store the Distance D and the Angle e, respectively. If an x,y coordinate system is being used, such as the exemplary coordinate system illustrated in FIG. 7d, at Block H an operator inputs an electrode number, which is accepted and stored by the Signal Processor 16. Blocks I and J are then executed to input, accept, and store the x and y coordinates respectively. If another two dimensional coordinate system is being used (OTHER), at Block K an operator inputs an electrode number, which is accepted and stored by the Signal Processor 16. Blocks L and M are then executed to input, accept, and store the first and second coordinates, respectively. At Block E a determination is made if a further electrode is to be entered. If NO, control passes to Block F where the electrode entry routine is terminated. If YES at Block E, control returns to either Block B, H, or K to enter the next electrode number.

Figure 8A:
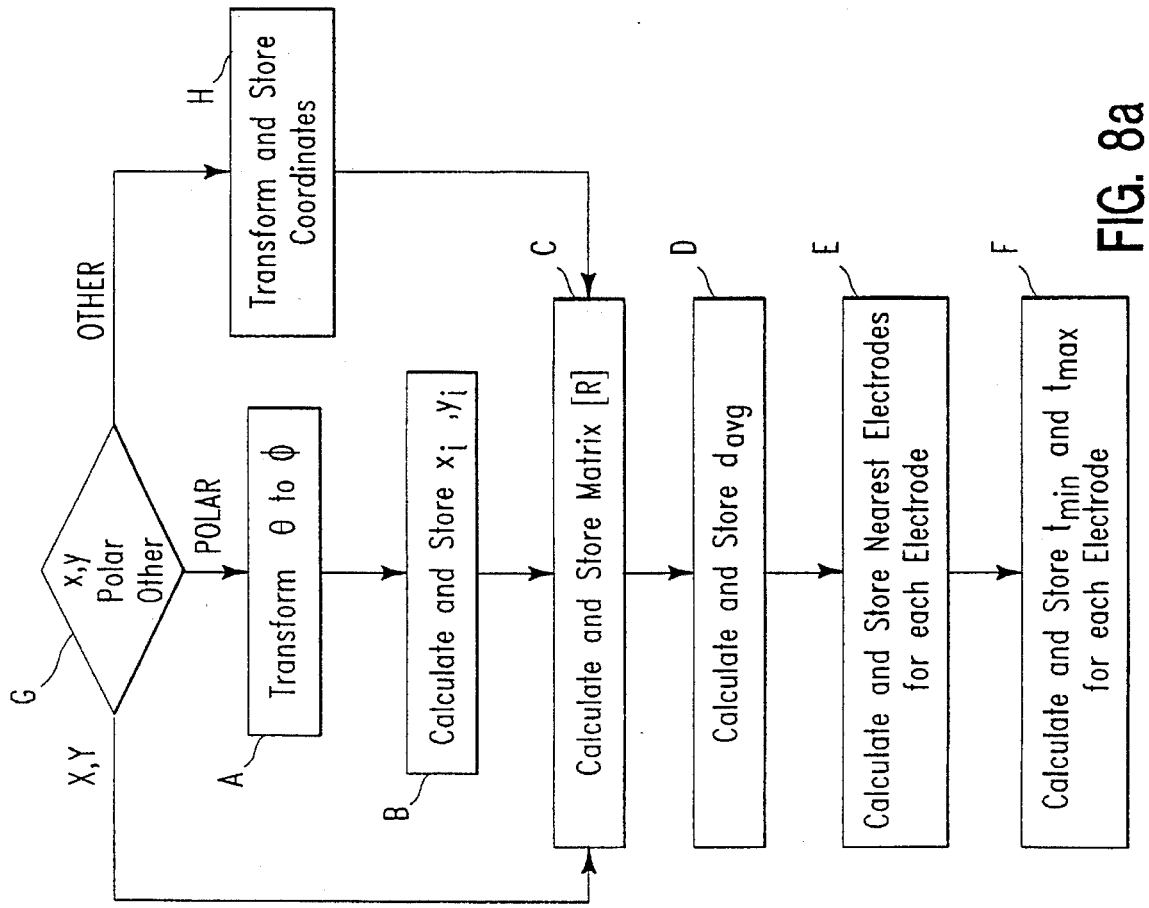
FIG. 8a is a logic diagram of a method for determining the nearest electrodes to each electrode, and the maximum and minimum transit time of electrical activity from the first electrode to each of these nearest electrodes.

After all of the electrode coordinates have been entered, in accordance with the logic diagram of FIG. 8, mathematical operations are performed upon these coordinates in accordance with the logic diagram of FIG. 8a.

At Block G, the microprocessor determines the type of coordinate system based on the value entered by the operator in Block N of FIG. 8. If a polar coordinate system is chosen, control passes to Block A.

In Block A, the angular coordinate e is transformed to $\phi$. Let $r_i$ and $e_i$ be the coordinates of $e_i$ (the $i^{th}$ electrode), measured as described previously. Then, transform the angular coordinate θ to $\phi_i$ so that the angle is measured from a horizontal x axis. The y axis is vertical and is perpendicular to the x axis. The transformation of $\phi_i = 90 - \theta_i$.

In Block B, the x and y $(x_i, y_i)$ coordinates of $e_i$ are then calculated as:

$$x_i = r_i \cos \phi_i$$

$y_i = r_i \sin \phi_i$ and the result of the calculation is stored.

The distance $r_{ij}$ between two electrodes $e_i$ and $e_j$ is then given by:

$$r_{ij} = [(x_i - x_j)^2 + (y_i - y_j)^2]^{1/2}.$$

In Block C, the symmetric matrix [R] whose components are the distances $r_{ij}$, where $r_{ii} = 0$ and $r_{ij} = r_{ji}$, is constructed and stored.

In Block D, the average interelectrode distance, $d_{avg}$, is determined. First, sort the matrix [R] into the vector D. Let $d_j$ be an element of this vector. Starting from the smallest distance, examine the value of the variable $del_j = d_j - d_{j-1}$, then calculate a running average of the value of del, which is referred to as $del_{avg}$. When $del_j > 3 \cdot del_{avg}$, the average interelectrode distance is given by $$d_{avg} = (d_1 + \ldots + d_{j-1})/(j-1).$$

In Block E, the nearest electrodes to a given electrode, $e_i$, are determined. First sort the distances $r_{ij}$. If $d_{avg}$ is the average interelectrode spacing, then the nearest electrodes are those electrodes which are within $f \cdot d_{avg}$ of $e_i$, where f is a factor in the range of 1 to 2, and typically has a value of 1.5.

In Block F, the maximum and minimum times for electrical activity to reach a given electrode are calculated and stored. Let $V_{max}$ and $V_{min}$ be the maximum and minimum observed propagation rates of electrical activity. For an interelectrode spacing of $r_{ij}$, the minimum time for $V_{min}$ is 0.7 cm/sec and $V_{max}$ is 6 cm/sec. electrical activity to reach electrode j is $r_{ij}/V_{max}$. Conversely, the maximum time is $r_{ij}/V_{min}$. Typically, $V_{min}$ is 0.7 cm/sec and $V_{max}$ is 6 cm/sec.

Turning again to Block G of FIG. 8a, if an x,y coordinate system is chosen, control passes to Block C (with the above given logic), and then to the remaining blocks in the logic flow diagram. If another coordinate system is chosen (OTHER), control passes to Block H, which contains the appropriate logic for the transformation of that coordinate system to an x,y coordinate system. The result of that calculation is then stored. Control then passes to Block C where the matrix [R] is calculated and stored, and then to the remaining blocks in the logic flow diagram.

Referring again to FIG. 2, the signals generated by each of the measurement electrodes, for example E1 and E2, serve as the input to the associated amplifier 14a. Preferably, the amplifier 14a is a differential amplifier having the following (typical) characteristics:

Input Impedance: >10 M ohms in parallel with 5 pF

High Pass 2nd order: 0.01 Hz cut off frequency

Notch filter: 3 dB pass band of 1.6 Hz, minimum 40 dB attenuation, at line frequency Input: 5–300 microvolts Noise: 1.3 microvolts peak to peak (maximum) over bandwidth (0.01–200 Hz)

Output: 100 mv minimum

CMRR: >80 dB at line frequency

Gain: 20,000

Band Width: 0.01–200 Hz.

The output of the amplifier 14a is input to the Envelope Detector 14b, which may be analog or digital, and which functions to derive the envelope of the amplified electrode signal as seen in the lower trace of FIG. 1b. As was noted above, the Envelope Detector 14b may be embodied in a low pass filter. The output of the Envelope Detector 14b provides a first display (DISPLAY1), and is input, via analog to digital conversion circuitry and suitable video processing circuitry, to the display monitor 18a. The output of the Envelope Detector 14a may also be provided to the strip chart recorder 18b. Other appropriate display means, known to those skilled in the art, can also be employed.

FIG. 1c illustrates an exemplary DISPLAY1 for the case where three measurement electrodes (E1, E2, E3) are provided. As can be seen, the envelope corresponding to the initiation of a contraction at the fundus appears at T1, and at T2 the contraction arrives at electrode E1 which is positioned near to the umbilicus. For a normal contraction, E3 can be expected to record the arrival of the contraction at time T3. However, if an abnormal condition is present the contraction may be recorded earlier (T4) or later (T5).

The output of each Envelope Detector 14b is also input to a corresponding Activity Detector processor 16a. The Activity Detector processor 16a detects electrical activity by analyzing points on the slope of the curve generated by the Envelope Detector 14b, and outputs a time (TIME) that such activity is detected, and the number of the electrode (ELECTRODE #) that detected the activity.

Figure 9:
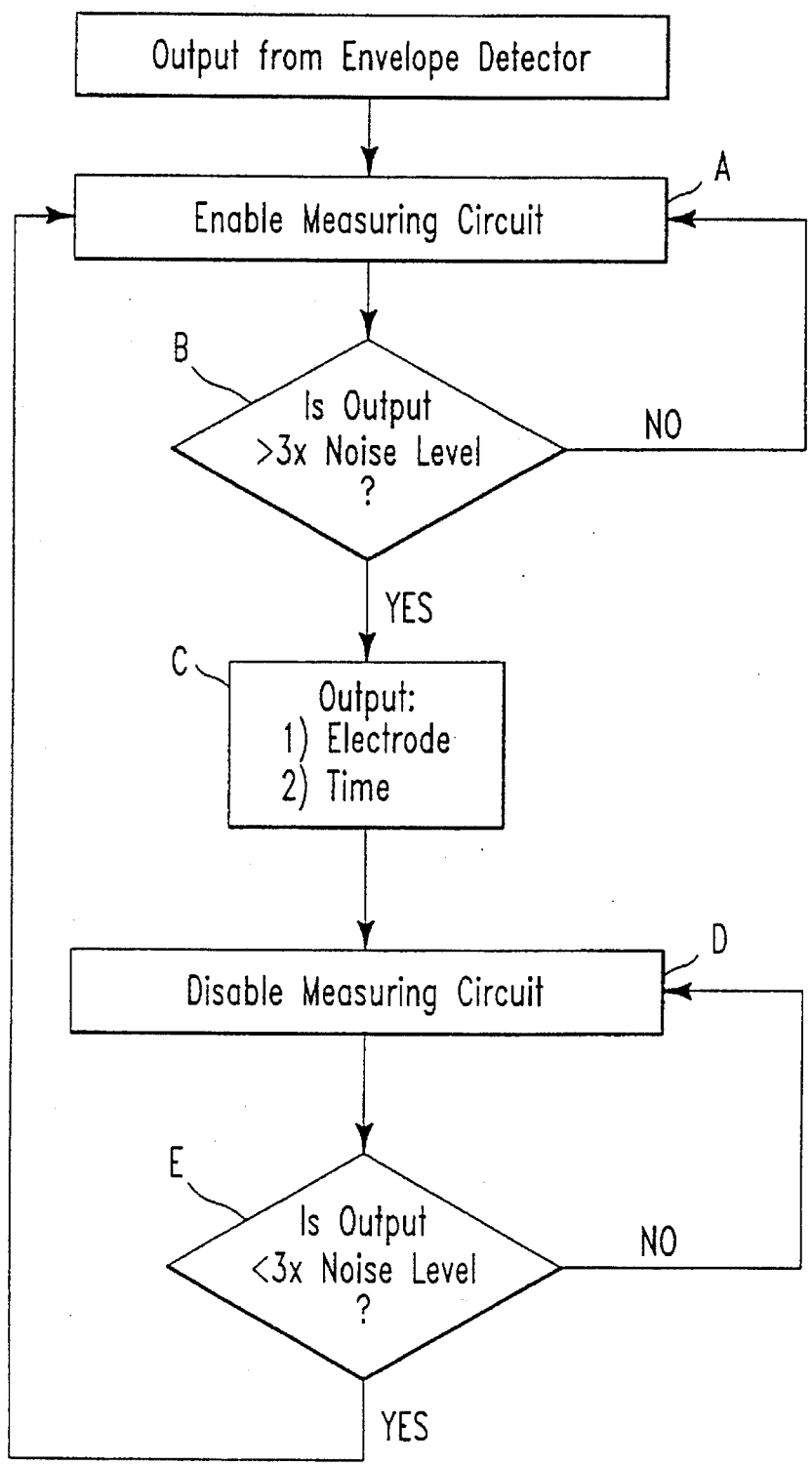
FIG. 9 is a logic diagram of a method for operating an Activity Detector processor of FIGS. 2, 3, and 4.

The logic flow diagram of FIG. 9 illustrates the operation of the Activity Detector processor 16a. At Block A an internal measuring circuit is enabled to receive the output from the Envelope Detector 14b. At Block B a determination is made if the output of the Envelope Detector is greater than some multiple of an inherent noise level. By example, one suitable multiple is three times the level of the noise. If NO at Block B, control returns to Block A to maintain the measuring circuitry enabled. If YES at Block B the Activity Detector processor 16a outputs the associated electrode number and a time at which the output exceeded the multiple of the noise level. At Block D the measuring circuitry is disabled, and at Block E a determination is made if the output of the Envelope Detector has dropped below the multiple of the noise level. If NO at Block E, control returns to Block D to maintain the measuring circuitry disabled. If YES at Block E, control passes to Block A to reenable the measuring circuitry so as to detect the electrical signal resulting from the occurrence of a next contraction at the associated electrode.

The output of two of the Activity Detector processors 16a is provided to the Vector Determination processor 16b, which is initially programmed with the identifiers and the coordinates of each of the electrodes (FIG. 8). In general, if $t_{min} < T < t_{max}$ (where [$t_{min}$, $t_{max}$] is the time interval in which electrical activity would be expected to move between two electrodes ($E_i$ and $E_j$) separated by a distance D), the Vector Determination processor 16b determines V, the Contraction Vector. The magnitude of the Contraction Vector is the rate of progression of the electrical activity, and the direction is the polar coordinate $\theta$ of $E_j$ with respect to $E_i$.

Figure 10A:
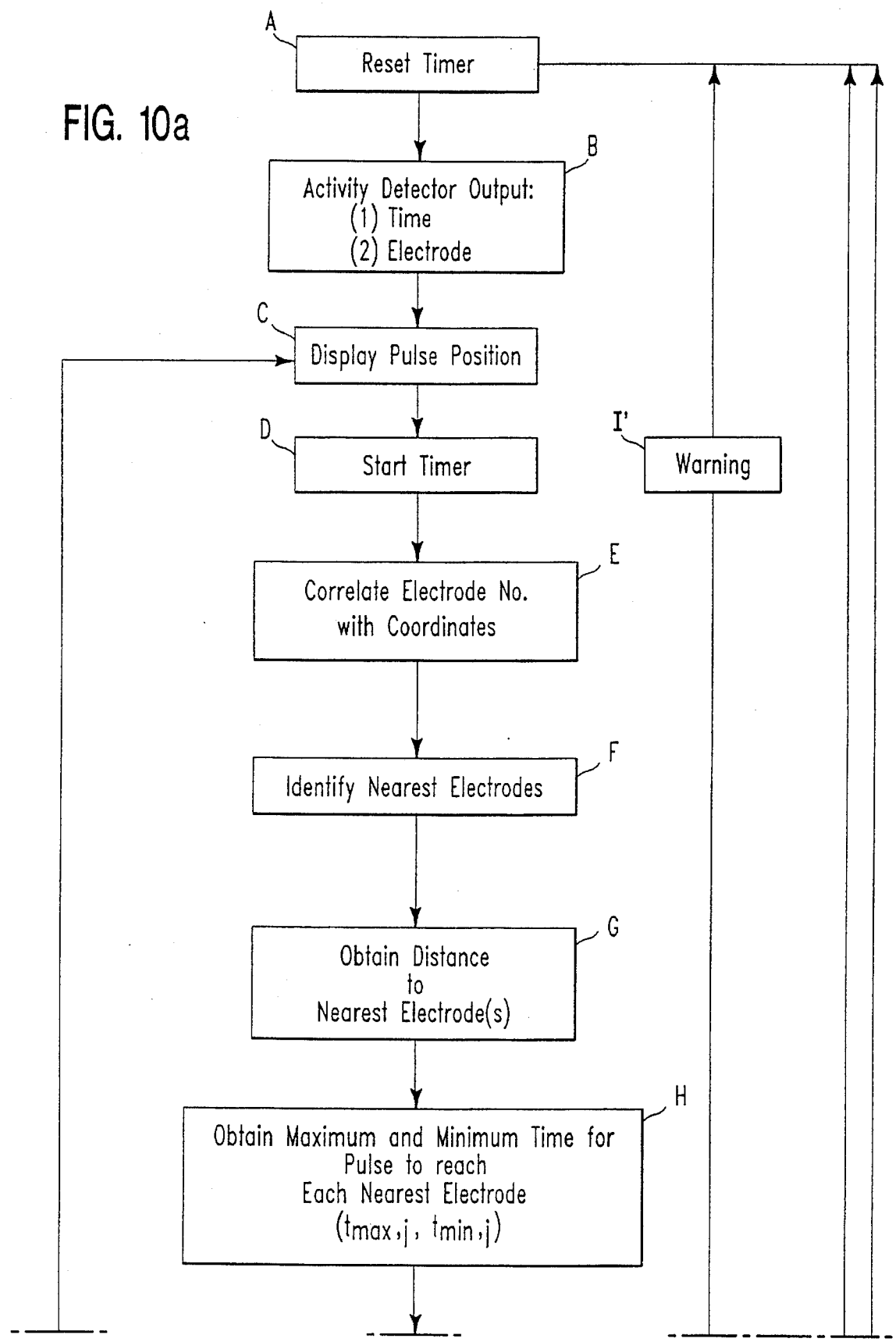
Figures 10, 10A, 10B:
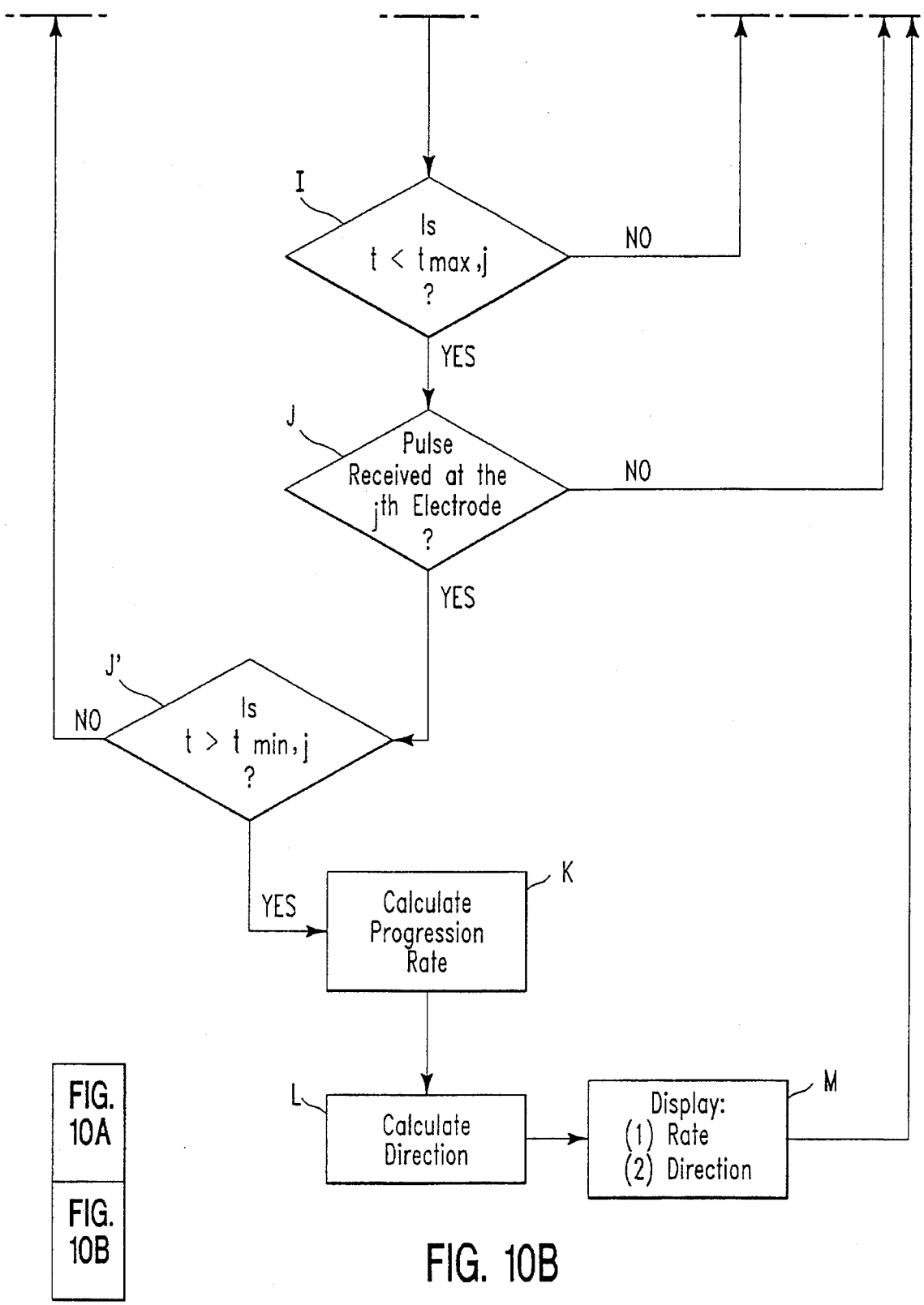

FIG. 10 is a logic flow diagram of the operation of the Vector Determination processor 16b. At Block A an internal timer is reset. At Block B the output of one of the Activity Detector processors 16a is received. At Block C the pulse position is displayed (DISPLAY2, FIG. 1d(a)) and at Block D the internal timer is started. At Block E the electrode number received from the Activity Detector processor 16a is correlated with the position coordinates that were previously inputted and stored (FIG. 8). At Block F the identity of the electrode or electrodes that are nearest to the currently identified electrode is determined.

By example, and referring to FIG. 7b, the electrodes nearest to electrode E2 are electrodes E7, E1, and E3, while the electrodes nearest to electrode E1 are the electrodes E2–E7. By including and monitoring electrodes above and below E1, the LDS 10 is enabled to determine a propagation direction of a contraction in any direction from E1. As is well known, in early labor a contraction may originate at any point on the uterus, and may propagate in any direction.

Returning to FIG. 10, at Block G, the distance to the nearest electrode(s) is obtained from storage. At Block H a maximum ($t_{max}$) and minimum ($t_{min}$) time is determined for the contraction pulse to arrive at each of the identified nearest electrodes, based on the distance determination of Block G. At Block I a determination is made if the elapsed time from the starting of the timer at Block D is less than $t_{max}$. If NO, indicating that a time equal to $t_{max}$ has expired, control returns to Block A. Optionally, at Block I' a warning indication may be generated to indicate that the contraction did not arrive at the $j^{th}$ electrode. This condition may or may not indicate an abnormality, in that in the early stages of labor a contraction may not propagate completely from the fundus to the isthmus of the uterus. As such, it may be desirable to enable the operation of Block I' only during the later stages of labor. As will be made apparent below, this determination may be made automatically by the LDS 10 from, for example, the time between successive contractions and/or the output of the cervical dilation processor 16d.

If YES at Block I, a determination is made at Block J if the contraction pulse has been received at the $j^{th}$ electrode, as determined from the outputs of the associated Activity Detector processor(s) 16a. If NO, control returns to Block A. If YES at Block J a determination is made at Block J' if the elapsed time is greater than $t_{min}$. If YES at Block J' a calculation is made of the progression rate of the contraction between the electrode identified at Block B and the $j^{th}$ electrode. If NO at Block J', indicating that the electrical activity sensed at the $j^{th}$ electrode is independent from that sensed by the electrode identified in Block B, control returns to Block C. The electrical activity is then treated as independent to that sensed at the electrode identified in Block B. The progression rate is determined by using the Time received at Block B and the Time output by the $j^{th}$ Activity Detector processor 16a, and the distance $r_{ij}$ between the two electrodes. The calculation is performed as follows: If electrical activity is sensed at electrode $e_i$ at time $t_i$, and if within $t_{max}$, electrical activity is sensed at electrode $e_j$ at time $t_j$, and the distance between $e_i$ and $e_j$ is $r_{ij}$, then the progression rate of the activity, $p_{ij}$, is $$p_{ij}=r_{ij}/(t_j-t_i).$$

At Block L, a calculation is made of the direction of the contraction propagation based on the stored values of e for the identified electrodes. At Block M, the Vector Determination processor, 16b, displays, as DISPLAY2, the calculated progression rate and direction of the contraction.

As seen in FIG. 1d(a), the contraction propagation vector V is shown for a contraction propagating from E2 to E1. The direction is indicated by the arrow labelled V, and the rate is numerically shown as, by example, 1.8 cm/sec. FIG. 1d(b) shows the DISPLAY2 at a later point in time and shows the continuation of the contraction propagation vector from E1 to E3 at a rate of 1.7 cm/sec.

FIG. 1e illustrates the DISPLAY2 for a case wherein a constellation of significantly more than three measurement electrodes are applied to the patient, and wherein a contraction propagates in a normal fashion from the fundus to the cervix. FIG. 1f illustrates the DISPLAY2 for the electrode configuration of FIG. 1e, but where the uterine contraction propagates abnormally. This abnormal propagation of the contraction may indicate a pathological condition, and is of great benefit to the practitioner observing the display monitor 18a.

Figure 5:
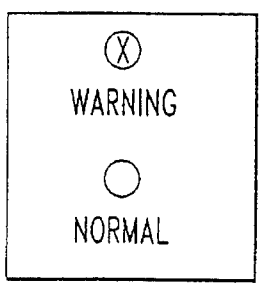
FIG. 5 is an example of a display (DISPLAY3) of the change in the rate of movement of uterine activity, as detected by the embodiment of FIG. 2, to indicate a normal or abnormal condition.
Figure 3:
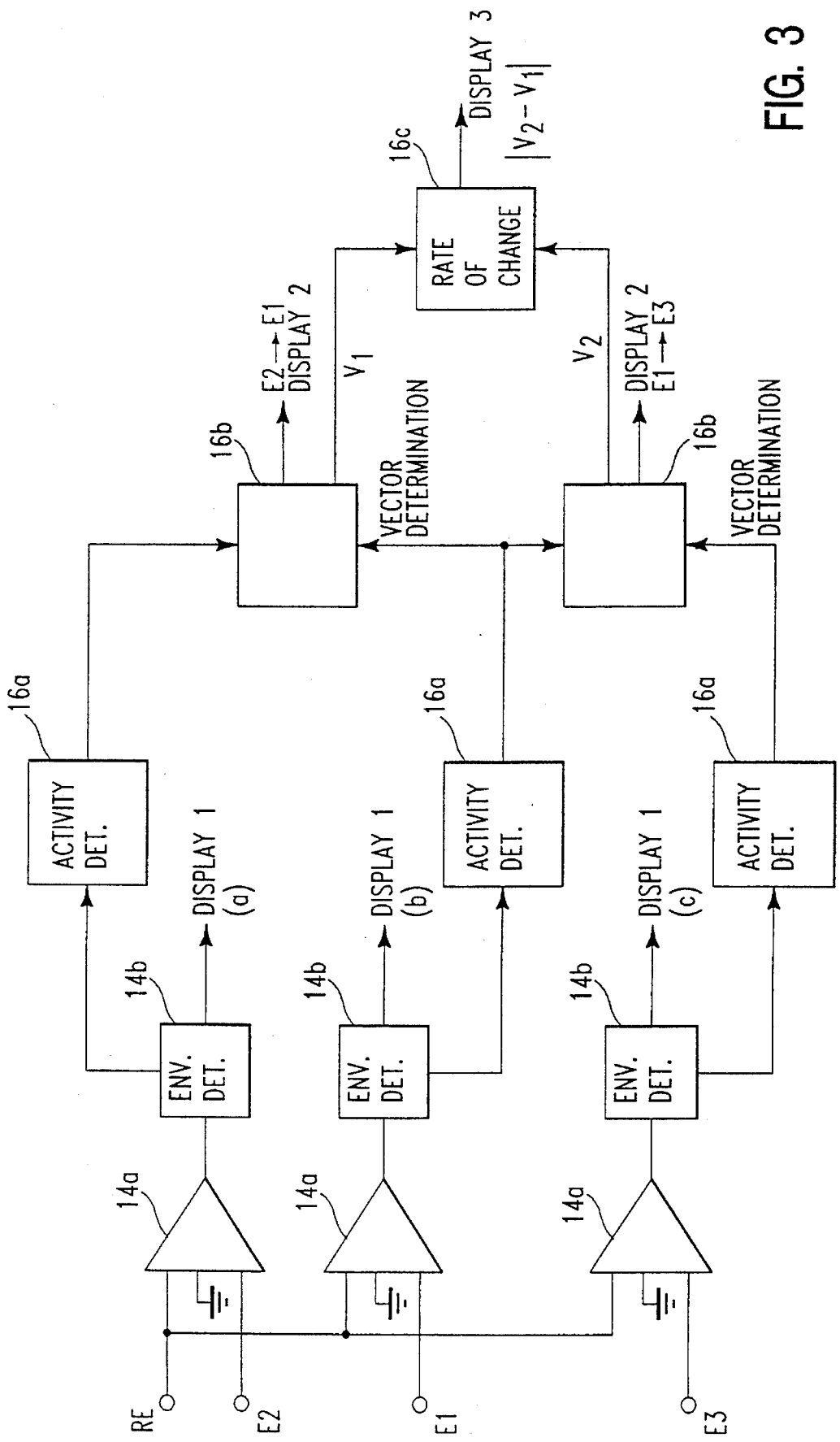
FIG. 3 is a block circuit diagram of a second embodiment of the apparatus according to the invention, in which further circuitry is provided to determine and display changes in a rate of movement of uterine activity.

A second embodiment of the LDS 10 is shown in FIG. 3, wherein components that operate as in FIG. 2 are numbered accordingly. This embodiment illustrates a third amplifier 14a, Envelope Detector 14b, and Activity Detector processor 16a for receiving and processing the signal received from the third electrode E3 of FIG. 7a. A second Vector Determination processor 16b receives inputs from the Activity Detection processors 16a for the electrodes E1 and E3. FIG. 3 further shows a Rate of Change processor 16c which receives inputs from the two Vector Determination processors 16b, specifically the magnitudes |V1| and |V2| of the contraction vectors sensed by two adjacent electrode pairs. The Rate of Change processor 16c determines from these inputs a difference |V2–V1|, and provides a DISPLAY3, as shown in FIG. 5. If |V2–V1|> lim, where lim is an acceptable change in the magnitude of the contraction vector, a Warning signal is generated, otherwise a Normal indication is displayed.

Figure 11:
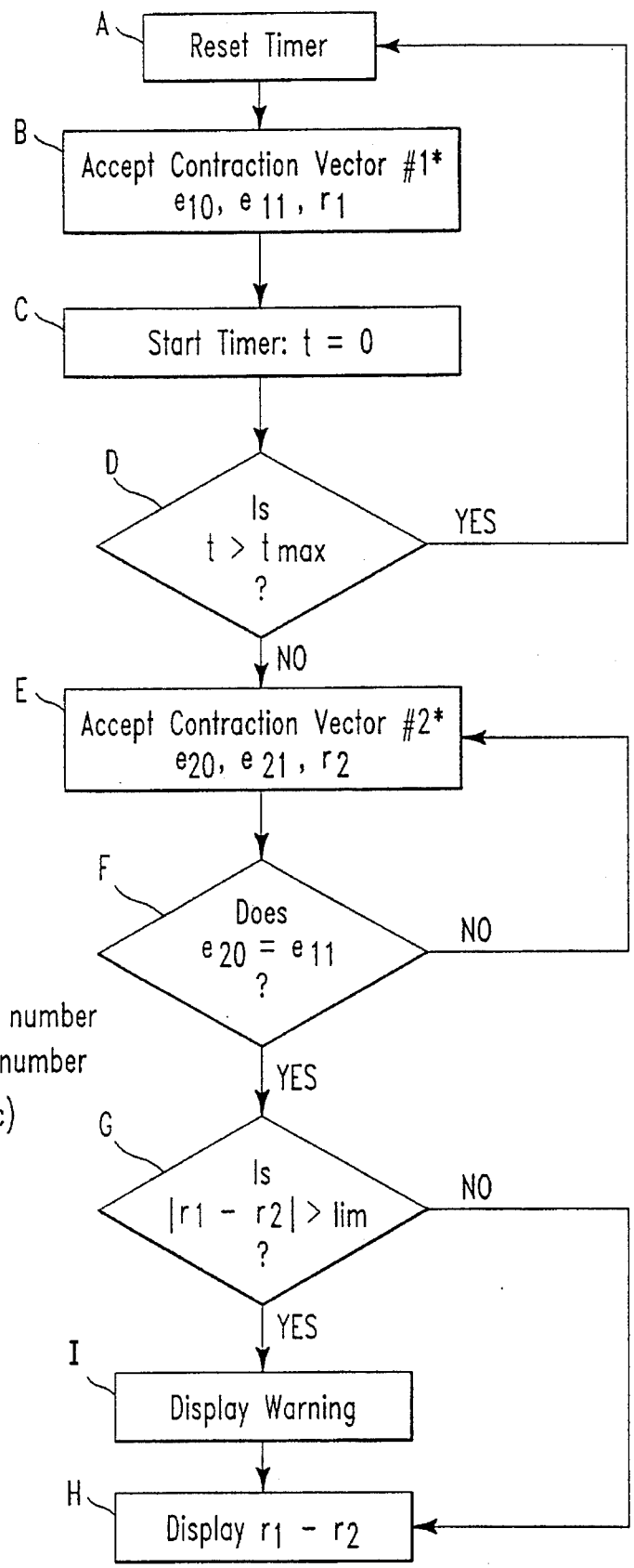
FIG. 11 is a logic diagram of a method for operating a Rate of Change processor of FIG. 3.

FIG. 11 is a logic flow diagram that illustrates the operation of the Rate of Change (ROC) processor 16c. At Block A an internal timer is reset. At Block B the ROC processor 16c accepts a first contraction vector from one of the Vector Determination processors 16b. In response to the receipt of the first contraction vector the internal timer is started (Block C). At Block D a determination is made if an elapsed time is greater than a predetermined maximum time. If YES, control returns to Block A and the timer is reset. If NO, control passes to Block E where a second contraction vector is received from one of the Vector Determination processors 16b. The information received from the Vector Determination processors 16b includes a starting electrode number, an ending electrode number, and a rate at which the contraction propagated between the starting and ending electrodes. At Block F a determination is made if the ending electrode number of the first accepted contraction vector equals the starting electrode number of the second accepted contraction vector. If NO a return is made to Block E to accept a further contraction vector. If YES at Block F, a determination is made at Block G if the rate of the first contraction vector differs from the rate of the second contraction vector by an amount greater than a predetermined limit. This determination is made by subtracting $r_2$ from $r_1$ and comparing the absolute value of the difference to the predetermined limit. If NO at Block G, the ROC processor 16c provides the Normal indication to DISPLAY3 at Block H, and may optionally graphically illustrate the difference between the two contraction rates. If YES at Block G, control passes to Block I where the Normal indication is extinguished and where the Warning indication is provided instead on the DISPLAY3. The Warning indication may be a visual indicator, an audible indicator, or a combination of these two. That is, if the propagation rates of two successive contractions are found to differ by more than a predetermined limit, a pathological condition may exist. The possibility of the existence of the pathological condition is thus visually and/or audibly indicated to the practitioner.

Figure 3A:
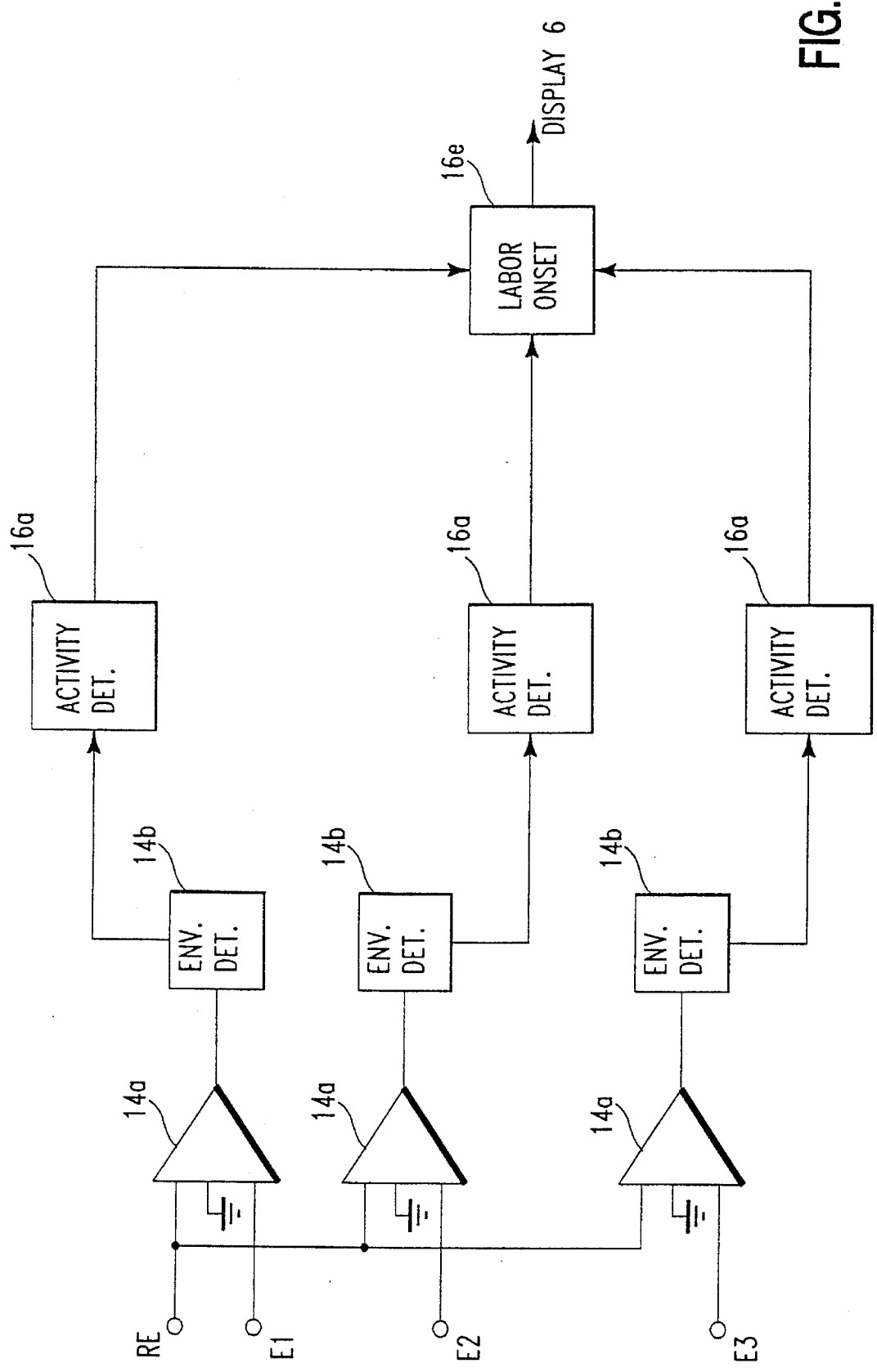
FIG. 3a is a block circuit diagram of a third embodiment of the apparatus according to the invention, in which circuitry is provided to detect uterine activity at a plurality of points, and in which circuitry is provided to determine the rate and periodicity of such activity to detect the onset of true labor.
Figure 13:
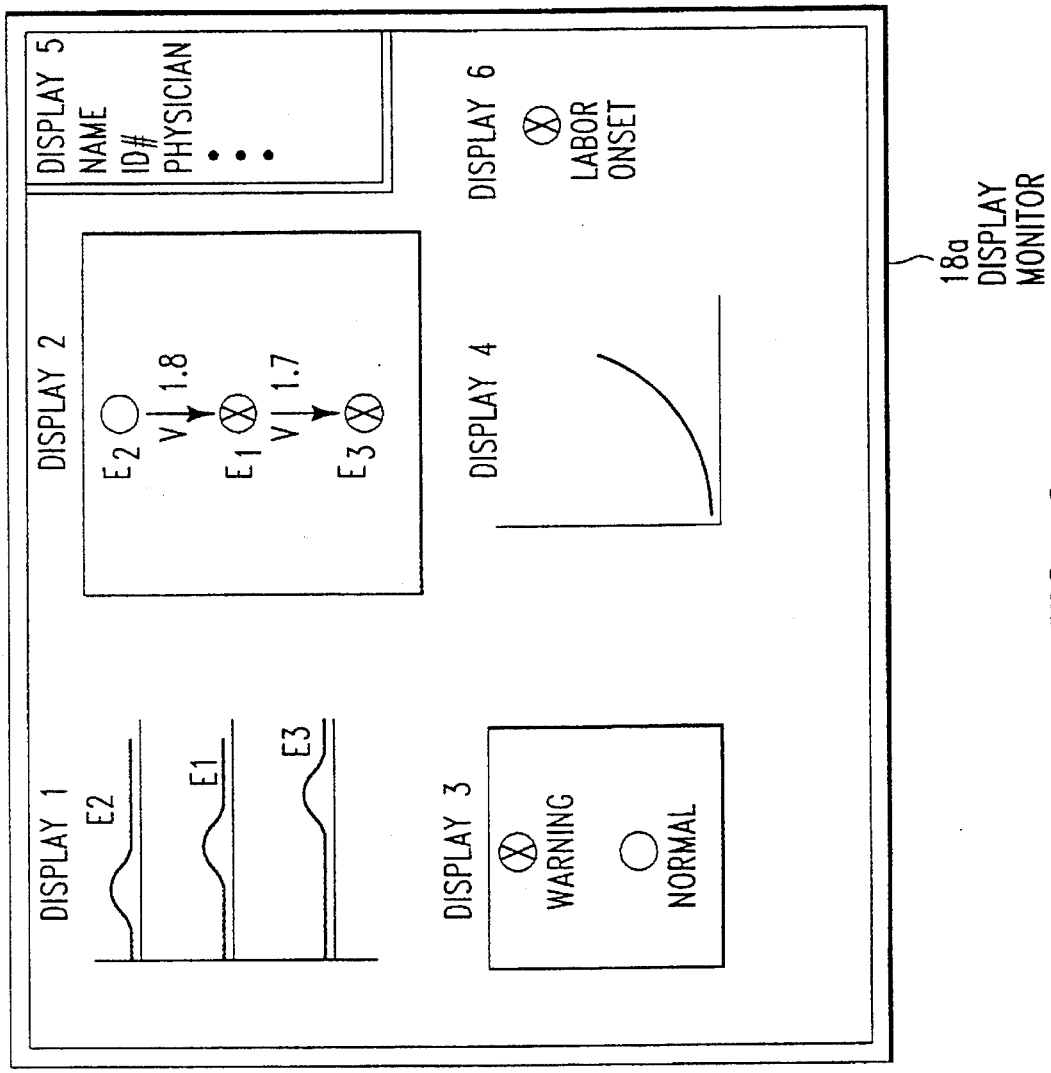
FIG. 13 illustrates a display monitor that simultaneously provides a plurality of displays of uterine contraction diagnostic information.

A further embodiment of the LDS 10 is illustrated in FIG. 3a wherein components that operate as in FIG. 2 are numbered accordingly. This embodiment is specifically an apparatus for determining the onset of true labor. This embodiment illustrates a third amplifier 14a, Envelope Detector 14b, and Activity Detector processor 16a for receiving and processing the signal received from the third electrode E3 of FIG. 7c. The outputs from the three Activity Detector processors, 16a, are input to a Labor Onset processor 16e. Specifically, the Labor Onset processor, 16e, determines if the sensed electrical activity is progressing from the uterine fundus to the cervix, and is of a periodic nature. An output of the Labor Onset processor 16e is provided as a DISPLAY6 for display on the monitor 18a, as shown in FIG. 13.

Figure 7C:
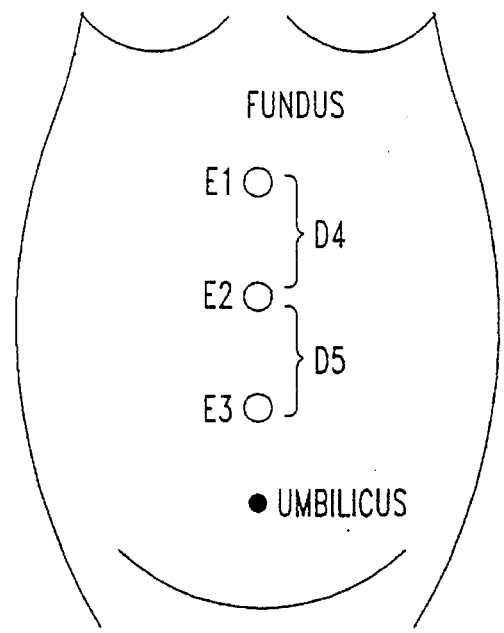
FIG. 7c is a diagram of a third possible electrode placement configuration.

For the operation of this embodiment of the invention, the electrode configuration as shown in FIG. 7c is used. Three electrodes, labeled E1, E2, and E3, are employed. All three are oriented in the vertical direction, with the top electrode being E1, the middle E2, and the bottom $E_3$. Preferentially, the electrodes are placed on a line extending from the umbilicus to the xiphoid, however, they can be positioned in other orientations known to those skilled in the art. The first electrode, $E_1$, may be positioned near the uterine fundus. The next two electrodes may be positioned in such a manner that the distance between $E_1$ and $E_2$ (D4) is the same as that between $E_2$ and $E_3$ (D5). By example, these distances may be 5 cm.

Figure 14A:
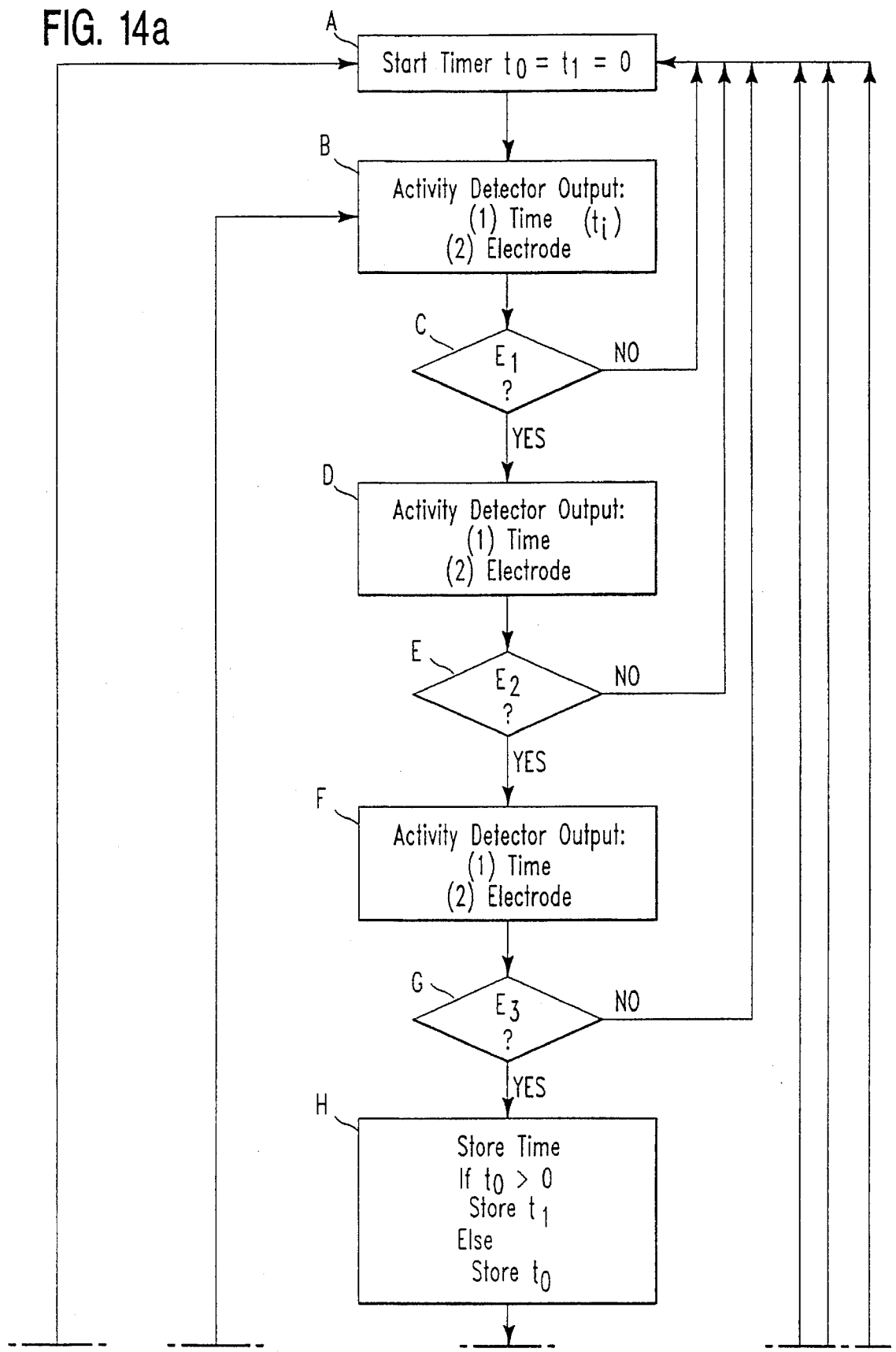
Figures 14, 14B:
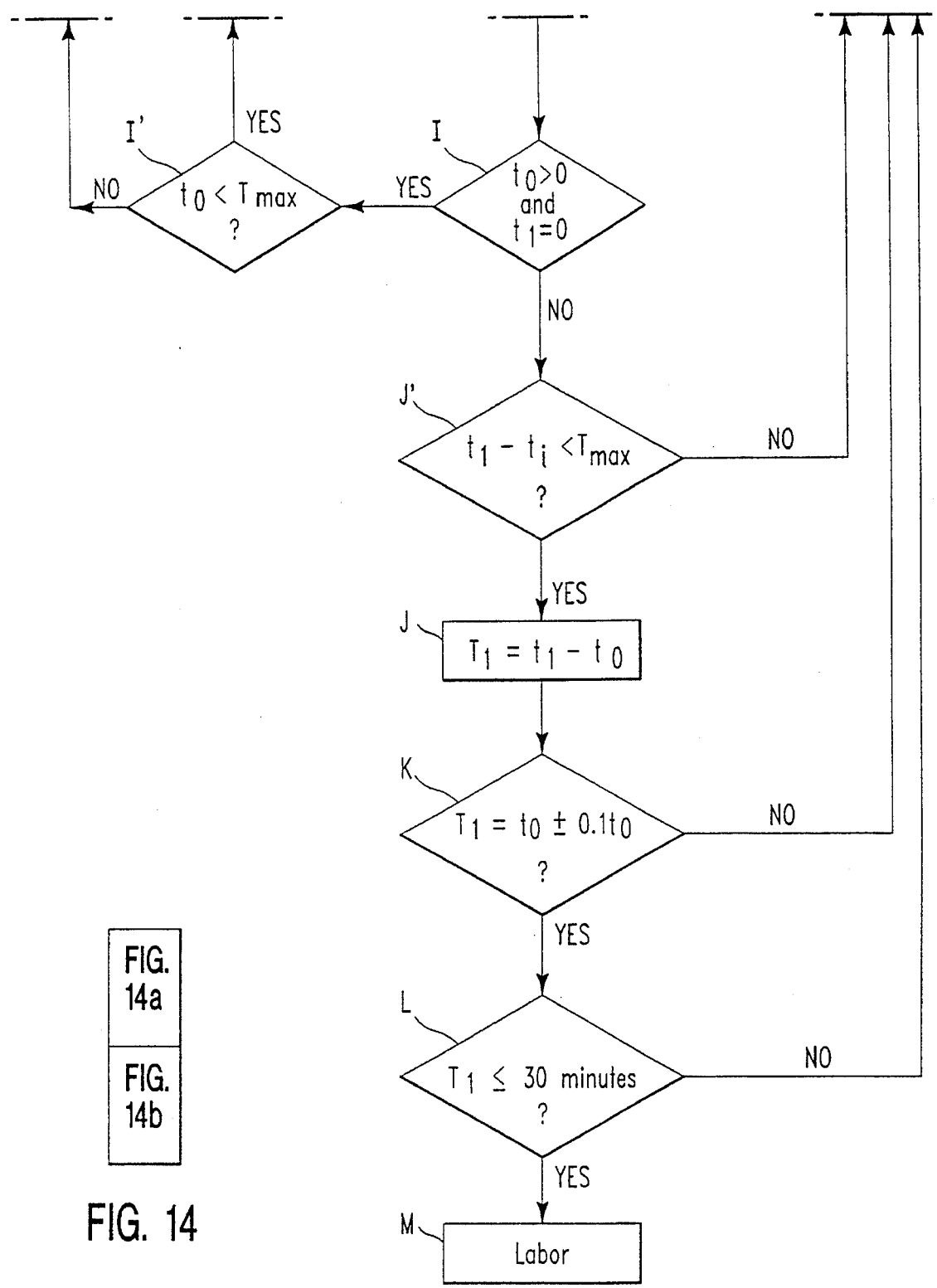

FIG. 14 is a logic flow diagram that illustrates the operation of the Labor Onset (LO) processor 16e. At Block A, an internal timer is initialized to zero. At Block B, the LO processor 16e accepts the output of an Activity Detector processor 16a. The initial time, $t_i$, is stored. At Block C, the LO processor 16e determines if the output is from the topmost electrode, $E_1$. If NO at Block C, control returns to Block A and the timer is reset. If YES at Block C, at Block D, the LO processor 16e accepts the output of an Activity Detector processor 16a. At Block E, the LO processor 16e determines if the output is from the middle electrode, $E_2$. If NO at Block E, control returns to Block A and the timer is reset. IF YES at Block E, at Block F, the LO processor 16e accepts the output of an Activity Detector processor 16a. At Block G, the LO processor 16e determines if the output is from the bottom electrode, $E_3$. If NO at Block G, control returns to Block A and the timer is reset. If YES at Block G, at Block H, the time which was output by the Activity Detector in Block F is stored by the LO processor 16e. If this is the first instance of activity, the time is stored as $t_0$. If not, the time is stored as $t_1$. AT Block I, a determination is made if this is the first instance of activity; i.e., $t_0>0$ while $t_1=0$. If YES at Block I, at Block I' the time a maximum time limit, $T_{max}$. The value of $T_{max}$ is a interval from the first to the last of the three outputs from the Activity Detector processors 16a is compared to a maximum time limit, $T_{max}$. The value of $T_{max}$ is a function of the spacing between $E_1$ and $E_3$, and is calculated as in Block F of FIG. 8a. If NO at Block I', control returns to Block A and the timer is reset. If YES at Block I', control returns to Block B to accept the next instance of electrical activity. If NO at Block I, indicating that this is a second instance of electrical activity, at Block J' the time interval from the first to the last of the three outputs from the Activity Detector processors 16a is compared to a maximum time limit, $T_{max}$. If NO at Block J', control returns to Block A and and the timer is reset. If YES at Block J', at Block J, a calculation is made of the time interval, $T_1$, between the two instances of electrical activity. At Block K, a determination is made if the two instances of electrical activity occurred within a certain percentage of each other, typically 10%. If NO at Block K, indicating that the electrical activity is of a random nature, control returns to Block A and the timer is reset. If YES at Block K, at Block L a determination is made if the two episodes of electrical activity occurred within a minimum time frame, for example 30 minutes. If YES at Block L, at Block M the LO processor 16e indicates the onset of labor by an appropriate visible and/or audible warning. If NO at Block L, control returns to Block A and the timer is reset.

Figure 16:
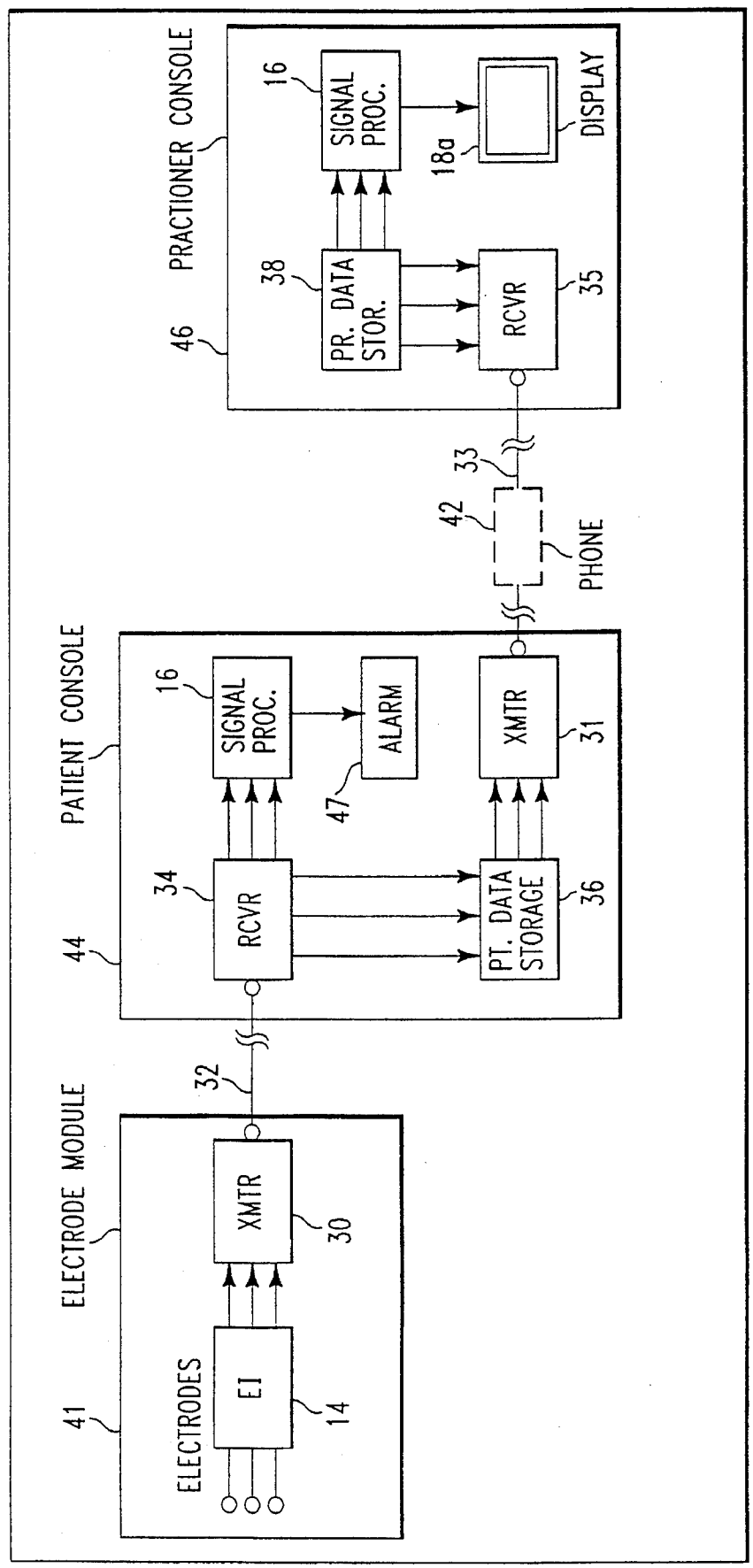
FIG. 16 is a block circuit diagram of a Labor Onset Alarm.

Furthermore, the embodiments of the invention shown in FIGS. 3a, 7c, and 14 can be combined to to construct and operate, in accordance with a further aspect of the invention, a Labor Onset Alarm (LOA) 8, as shown in the block circuit diagram of FIG. 16.

The LOA 8 includes three major sub-systems, specifically an electrode module 41, a patient's console 44, and a practitioner's console 46. The electrode module 41 includes the electrodes that are attached to the patient, such as by the configuration shown in FIG. 7c, and the electrode interface 14. The output of the electrode interface is provided via a transmitter 30 over a communication link 32 to a receiver 34 that is contained within the patient's console 44.

The patient's console 44 includes the receiver 34 having outputs coupled to a signal processor 16 which, in turn, has an output coupled to an indicator or alarm 47. The receiver 34 also has outputs coupled to a patient data storage module 36 which, in turn, has outputs coupled to a transmitter 31.

In operation, the receiver 34 receives the data being transmitted through the communication link 32, the data being expressive of the progression of labor of the pregnant mammal to which the electrodes are attached. The acquired data is stored within the data storage module 36.

Reference is now made to FIG. 14. If YES at Block L, indicating that the LO processor 16e which forms a part of the signal processor 16 of the patient's console 44 has detected the onset of true labor, then the alarm 47 is activated to notify the patient. In response, the patient activates the transmitter 31 to transmit the data stored within the data storage module 36 over a communication link 33, such as a conventional phone line 42, to the practitioner's console 46.

The practitioner's console 46 includes a receiver 35 having outputs coupled to a data storage module 38 that provides temporary or permanent storage of the electrode data. Outputs of the data storage module 38 are provided to the signal processor 16 which operates as previously described. The Display 18a provides visual indications of the progression of the patient's labor to the practitioner.

After the data is received and stored in the data storage module 38 it is replayed into the signal processor 16, which processes the recalled data as described above and displays the results. The practitioner can then analyze the results to diagnose if true labor has begun. The practitioner is enabled to replay all of the recorded data or only certain selected segments thereof.

If the patient is being monitored by the LOA 8 within a hospital environment, then the patient's console 44 can be omitted and the data transmitted, via the communication link 32, directly to the practitioner's console 46 for analysis.

Figure 17:
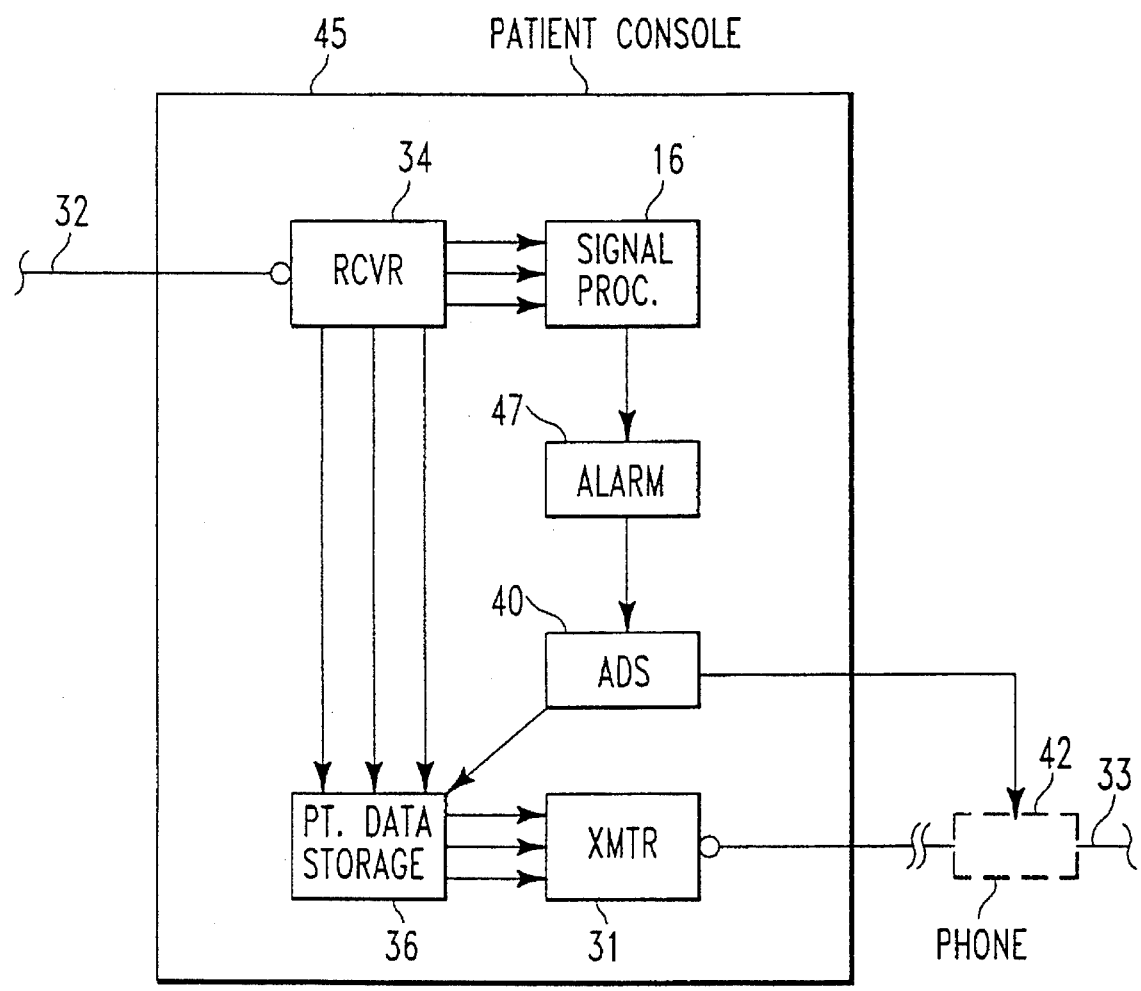
FIG. 17 is a block circuit diagram of an embodiment of a patient's console that forms a portion of the circuitry shown in FIG. 16.

FIG. 17 illustrates a further embodiment of a patient's console 45. This embodiment includes, in addition to the alarm 47, an automatic dialing system (ADS) 40. In response to the LO processor 16e detecting the onset of true labor, the alarm 47 is activated and the ADS 40 automatically establishes communications between the data storage module 36 and the practitioner's console 46. Upon establishment of communications through the communication link 33, the ADS 40 triggers the data storage module 36 to replay the stored electrode data, via transmitter 31, telephone interface 42, and communication link 33, to the receiver 35 of the practitioner's console 46.

The data storage modules 36 and 38 are embodied within any suitable storage systems for storing a digital or an analog representation of the electrode data. By example, the patient's console 44 data storage module 36 has a storage capacity suitable for storing up to six hours of continuously or intermittently sampled electrode data. The practitioner's console 46 may have a significantly larger storage capacity for storing multiple transmissions from a single or multiple patient consoles 44.

Figure 4A:
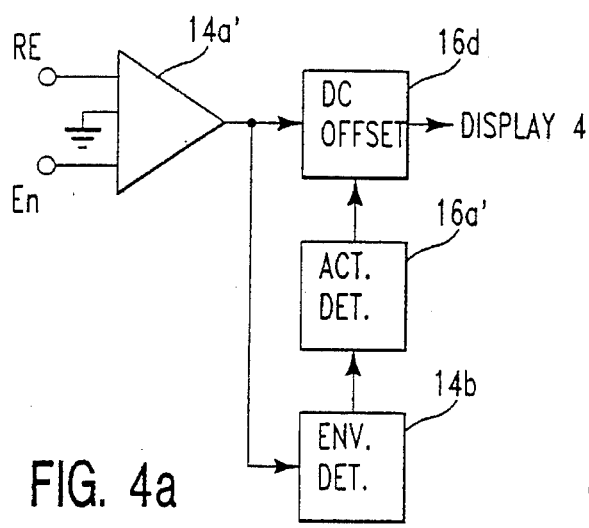
FIG. 4a is a block circuit diagram of a fourth embodiment of the apparatus according to the invention, in which circuitry is provided to detect and display an extent of cervical dilation.

A further embodiment of the LDS 10 is illustrated in FIG. 4a, specifically an apparatus for determining an extent of cervical dilation. This embodiment exploits a realization by the inventor that the extent of cervical dilation may be correlated with a detectable electrical signal and, more specifically, with a DC offset of the electrical signal, and that this information may be displayed in a meaningful way. As cervical dilation increases during the progress of labor, the DC offset increases correspondingly.

This embodiment of the invention includes an Envelope Detector 14b and an Activity Detector processor 16a'. The Activity Detector processor operates similarly to the Activity Detector processors 14a as in the embodiments of FIGS. 2 and 3. However, the Activity Detector processor 16a' is employed to determine when a contraction is not in progress, and it is during this time that the DC offset signal is sampled, as seen in FIG. 4b.

The embodiment of FIG. 4a also includes an amplifier 14a' having characteristics similar to those of the amplifiers 14a of FIGS. 2 and 3, except that the output is DC coupled to the input. The output of the DC coupled amplifier 14a' is split into two paths. The first path is coupled to the Envelope Detector 14b. The second path is coupled to a DC Offset processor 16d which determines a DC offset of a signal obtained from an electrode E(n) when electrical activity, indicative of a contraction, is not being sensed. Preferably, E(n) is externally affixed to the patient so as to overlie the cervix. The action of the DC Offset processor 16d is controlled by the output of the Activity Detector processor 16a. An output of the DC Offset processor 16d provides the DISPLAY4, as shown in FIG. 6.

Figure 6:
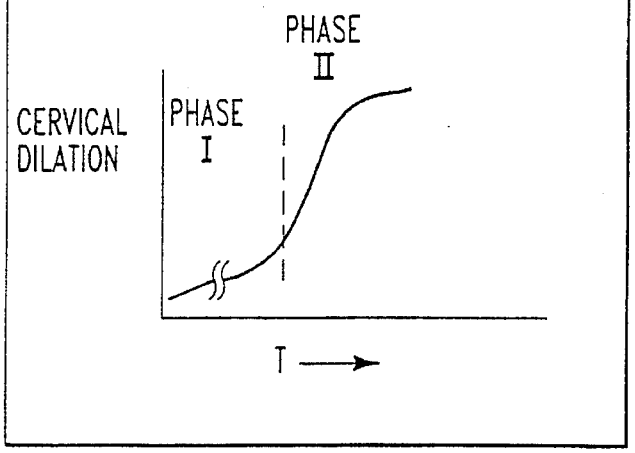
FIG. 6 is an example of a display (DISPLAY4) of cervical dilation, as detected by the embodiment of FIG. 4.

In FIG. 6, the extent of cervical dilation can be seen to increase at a first rate during a period referred to as Phase I of labor. Phase I may last for some indeterminate period of time from several minutes to several tens of hours. The onset of Phase II of labor is indicated by an increase in the rate of cervical dilation, the extent of dilation increasing up to some maximum point at which the patient is fully dilated. As such, the information conveyed by DISPLAY4 is also of great use to the practitioner in monitoring the progress of the patient's labor.

Figure 4B:
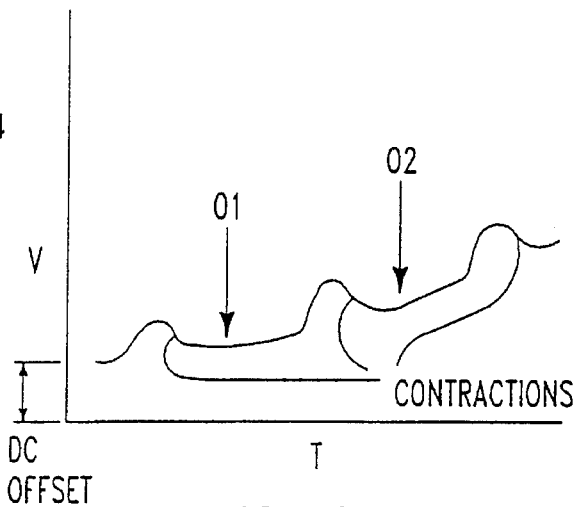
FIG. 4b graphically illustrates the points at which the embodiment of FIG. 4a samples an electrical signal that is indicative of the extent of cervical dilation.
Figure 12:
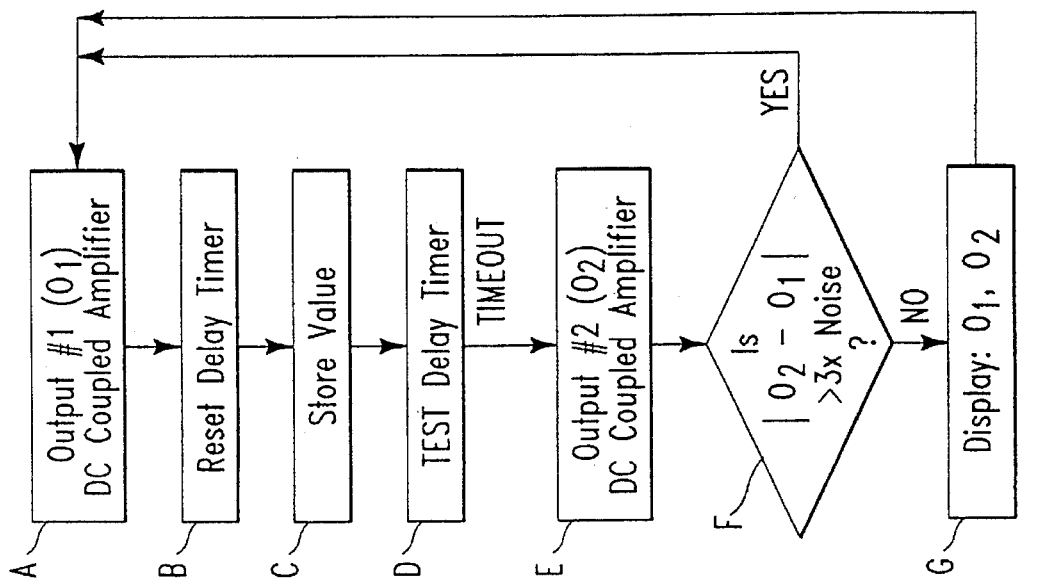
FIG. 12 is a logic diagram of a method for operating a DC Offset processor of FIG. 4.

FIG. 12, intended to be read in conjunction with FIG. 4b, is a logic flow diagram that illustrates the operation of the DC Offset processor 16d, in cooperation with the Activity Detector processor 16a, of FIG. 4a. At Block A an output #1 ($O_1$) is obtained from the DC coupled amplifier 14a'. A delay timer is reset at Block B and $O_1$ is stored at Block C. At Block D the delay timer is tested for a timeout condition. The delay timer value may be set to timeout, by example, once per minute. That is, because of the relatively slow rate of change of the cervical dilation, it is typically not necessary to sample the electrode E(n) at a rate of less than once per minute. The timeout value may be changed when Phase II of labor is entered, so as to sample the extent of cervical dilation more frequently.

At Block E a second output ($O_2$) of the DC coupled amplifier 14a' is obtained. At Block F a determination is made by the Activity Detector processor 16a', if the absolute value of $O_2-O_1$ is greater than some multiple, such as three, of the noise signal. If YES, it is indicated that a contraction is in progress and control returns to Block A. That is, the readings are discarded in that the DC offset is measured between contractions, and not during a contraction. If NO, the DISPLAY4 is updated at Block G by plotting the values of $O_1$ and $O_2$, with $O_1$ and $O_2$ indicating the DC offset voltage at two points in time and, hence, the degree of cervical dilation. Control then returns to Block A.

FIG. 13 illustrates an exemplary arrangement for the display screen of the display monitor 18a and shows a unified presentation of labor diagnostic information that is obtained by the LDS 10. If desired, a DISPLAY5 may be presented for showing information relating to the patient that is being monitored by the LDS 10. For example, when initially connecting the LDS 10 to the patient the practitioner may input the patient's name, patient number, physician's name, and any other relevant personal or medical information through the keyboard 20. This other information is then displayed, in conjunction with the DISPLAYS1–4 and 6, so as to provide the practitioner with detailed information regarding the patient and the progress of the patient's labor. In practice all, or only some, of the various DISPLAYS shown in FIG. 13 may be employed.

Although described above in the context of electrodes that are affixed to the patient in a predetermined pattern so as to best detect and monitor the progression of the uterine contraction, it should be realized that one or more other electrodes may be affixed at other positions. For example, for a case wherein the practitioner is aware that the placenta is implanted on the ventral wall of the uterus, as opposed to the dorsal wall, one or more electrodes may be affixed to the abdomen to overlie the placenta. In that the existence of contractions at that part of the uterus to which the placenta is attached may cause the placenta to become prematurely detached from the uterine wall, the electrical activity at these other electrode(s) is monitored and displayed so as to detect the existence of such contractions. For example, if a Vector Determination processor 16b indicates a contraction that propagates to an electrode that overlies the placenta, a Warning indication may be generated.

In summary, utilizing the LDS 10 as described above it is possible to measure the rate and direction of movement of the electrical activity of the uterine muscle. It thus becomes possible to distinguish true from false labor, in that true labor contractions always proceed from the fundus to the cervix. It also becomes possible to diagnose pathological labor conditions, wherein the movement of the electrical activity is unsynchronized or of the wrong direction.

Furthermore, in that it is known that undue stress on any part of the uterine muscle will produce abrupt changes in the rate of movement of the electrical activity of the uterine muscle in the region of the stress, it becomes possible for practitioners treating patients with previous cesarean sections to attempt normal deliveries without the fear of unexpected uterine rupture due to abnormal stress on the previous surgical scar, since any such stress is made readily apparent by the LDS 10.

Also, in that the direct current offset of the electrical activity of the uterine muscle can be related to the extent of cervical dilation, it therefore becomes possible to display the extent of cervical dilation on a continuous basis, without the use of any invasive procedure, and without much discomfort to the patient.

It should be realized that a number of modifications to the disclosed embodiments may be made while still obtaining the same or a similar results. For example, various ones of the components shown in FIGS. 2, 3 and 3a may be combined through the use of multiplexers and the like. For example, in FIG. 3 a single amplifier 14 may be provided having an input coupled through an analog multiplexer to the outputs of electrodes E1, E2, and E3. A similar multiplexer is then provided at the output of the single amplifier for directing the signal received from an electrode $E_i$ to a corresponding one of the Envelope Detectors $ED_1$. Also by example certain of the steps shown in the logic flow diagrams may be executed in other than the order shown. For example, in FIG. 10 Blocks C and D may be interchanged, as may Blocks K and L, while still obtaining the same result.

It should also be realized that the connection between the electrodes and the LDS 10 need not be through physical wiring, and that a suitable transmitter and receiver arrangement can be employed. This enables the remote monitoring of the patient via telemetry, as previously described with respect to FIGS. 16 and 17, to detect the onset and/or progression of labor, including the extent of cervical dilation and/or the presence of excessive stress on a part of the uterine muscle, without requiring that the patient be located in close physical proximity to the LDS 10. Suitable communications or telemetry links include, but are not limited to, modulated RF links and/or the transmission of a digital representation of the electrode signals over a telephone line.

Figure 15:
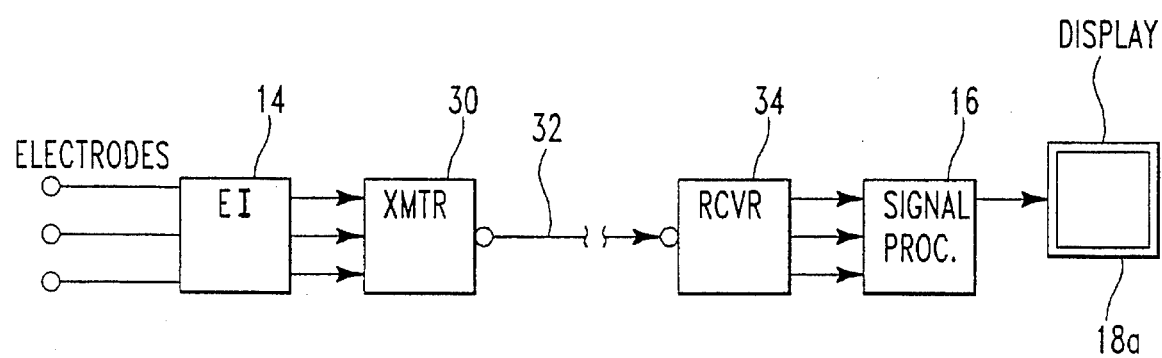
FIG. 15 is a block diagram illustrating an embodiment of the invention that provides for remotely monitoring a pregnant mammal over a communications link.

By example, and as is seen in FIG. 15, the electrodes may have a wired or a wireless connection with the electrode interface 14, which is disposed in proximity to the patient, and the output of the electrode interface 14 is provided via a transmitter 30, over a communication link 32, to a receiver 34, that is coupled to an input of the signal processor 16.

It should be further noted that the LDS 10 need not be dedicated to monitoring the labor of only a single patient. That is, suitable multiplexing techniques may be employed so as to provide a single signal processor, 16, that simultaneously receives inputs from, processes, and provides separate displays for a plurality of patients.

Thus, it will be understood that the above description of the present invention is amenable to various modifications, changes, and adaptations, and that these variations are intended to be comprehended within the meaning and range of equivalents of the appended claims. Thus, while the invention has been particularly shown and described with respect to several embodiments thereof, it will be understood by those skilled in the art that changes in form and details may be made therein without departing from the scope and spirit of the invention.

What is claimed is:

1. A monitoring system for use with a pregnant mammal, comprising:
   means for obtaining electrical signals from a plurality of superficial abdominal locations of a pregnant mammal, the electrical signals resulting from muscular activity-associated with labor;
   means, responsive to the electrical signals obtained from the plurality of superficial abdominal locations, for determining a uterine muscle contraction vector, the uterine muscle contraction vector having a propagation rate component and a propagation direction component with respect to at least a first superficial abdominal location, a second superficial abdominal location, and a third superficial abdominal location; and
   means for providing a visual representation of the determined uterine muscle contraction vector.

2. A monitoring system as set forth in claim 1, and further comprising:
   electrode interface means having a plurality of inputs for coupling to a plurality of electrodes that are affixed, during use, to the superficial abdominal locations of the pregnant mammal, the plurality of electrodes generating said electrical signals in response to a uterine muscle contraction, said electrode interface means having a plurality of outputs;
   input means for inputting a position of individual ones of said plurality of electrodes, the position being relative to a predetermined coordinate system that is referenced to a superficial abdominal region of the pregnant mammal; and
   means for storing said inputted electrode positions.

3. A monitoring system as set forth in claim 2 and further comprising:
   a plurality of envelope detector means, individual ones of which have an input coupled to one of said outputs of said electrode interface means, each of said envelope detector means having an output; and
   a plurality of electrical activity detector means, individual ones of which have an input coupled to one of said outputs of said plurality of envelope detector means, each of said electrical activity detector means having an output.

4. A monitoring system as set forth in claim 3 and further comprising:
   a plurality of vector determination means, individual ones of which have a first input coupled to an output of one of said electrical activity detector means and second input coupled to an output of a second one of said electrical activity detector means, each of said vector determination means having an output for outputting a signal that is indicative of a uterine muscle contraction that propagates between two electrodes.

5. A monitoring system as set forth in claim 4 wherein said signal output from each of said plurality of vector determination means is coupled to an input of said means for providing a visual representation.

6. A monitoring system as set forth in claim 4 and further comprising a vector change determination means having a first input coupled to said output of one of said plurality of vector determination means and a second input coupled to said output of another one of said vector determination means, said vector change determination means having an output for indicating a change in a rate of propagation or in a direction of propagation of one uterine muscle contraction vector with respect to another uterine muscle contraction vector.

7. A Monitoring system as set forth in claim 4 wherein said signal output from each of said plurality of vector determination means is coupled to an input of said means for providing a visual representation.

8. A monitoring system as set forth in claim 3 and further comprising:
   labor onset determination means having inputs coupled to said outputs of said electrical activity detector means and, responsive to said outputs, for generating a signal indicating a probable onset of labor.

9. A monitoring system as set forth in claim 3 wherein said signal output from each of said plurality of envelope detector means is coupled to an input of said means for providing a visual representation.

10. A monitoring system as set forth in claim 1 and further comprising:
    analog to digital conversion means, having an input coupled to an output-of said obtaining means, for converting the obtained electrical signals to a digital representation thereof; and
    memory means, having an input coupled to an output of said analog to digital conversion means, for storing the digital representation.

11. A monitoring system as set forth in claim 10 and further comprising:

communication means having an input coupled to an output of said memory means and an output coupled to an a communication link for transmitting the stored digital representation to a remote location over the communication link.

12. A monitoring system as set forth in claim 11 wherein said means for determining a uterine muscle contraction vector and said means for providing a visual representation of the determined uterine muscle contraction vector are located at the remote location; and wherein said means for determining a uterine contraction vector has an input coupled to the communication link for receiving the stored digital representation therefrom for determining the uterine muscle contraction vector in accordance with the received digital representation.

13. A monitoring System as set forth in claim 11 and further comprising:
   means, responsive to the detected electrical signals, for generating a signal indicating an onset of true labor; and
   means, responsive to the generated signal, for transmitting the stored digital representation to the communication link.

14. A monitoring system as set forth in claim 1 and further comprising:
   means for detecting electrical activity associated with an arrival of a uterine muscle contraction at a position associated With a first stored electrode position;
   means, responsive to the stored electrode positions, for identifying at least one other electrode;
   means for determining a maximum transit time for a uterine muscle contraction to propagate from the first electrode to the at least one other electrode; and
   means for monitoring the at least one other electrode for a period of time at least equal to the determined maximum transit time to detect electrical activity resulting from the arrival of the propagating uterine muscle contraction at the at least one other electrode; wherein
   said uterine muscle contraction vector determining means determines the propagation rate component and the direction component in response to the arrival of the propagating uterine muscle contraction at the at least one other electrode, wherein the propagation rate component is a function of a distance between the first electrode and the second electrode, and is also a function of a transit time of the propagating uterine muscle contraction between the first and second electrodes, and wherein the propagation direction component is indicative of the direction of a line between the first electrode and the second electrode.

15. A monitoring system as set forth in claim 1 and further comprising:
   means, responsive to the detected electrical signals, for determining an extent of cervical dilation.

16. A monitoring system as set forth in claim 15 wherein said interface means includes means for providing a DC interface with at least one electrode., and wherein said means for determining an extent of cervical dilation operates in response to electrical signals obtained from said at least one electrode.

17. A monitoring system for use with a pregnant mammal, comprising:
   means for periodically obtaining electrical signals from a plurality of superficial abdominal regions of a pregnant mammal, the electrical signals resulting from muscular activity associated with labor;
   means, responsive, to the obtained electrical signals, for determining if a contraction of the uterine muscle is in progress; and
   means, responsive to said determining means determining that a contraction is not in progress, for processing the obtained electrical signals, and for outputting an indication of an extent of cervical dilation.

18. A monitoring system as set forth in claim 17 wherein said obtaining means is comprised of means for providing a DC interface with at least one electrode, and wherein said means for determining an extent of cervical dilation operates in response to electrical signals obtained from said at least one electrode.

19. A monitoring system as set forth in claim 17 and further comprising:
   analog to digital conversion means, having an input coupled to an output of said obtaining means, for converting the obtained electrical signals to a digital representation thereof;
   memory means, having an input coupled to an output of said analog to digital conversion means, for storing the digital representation; and
   communication means having an input coupled to an output of said memory means, and an output coupled to a communication link, for transmitting the stored digital representation to a remote location over the communication link.

20. A monitoring system for use with a pregnant mammal, comprising:
   means for obtaining electrical signals from a plurality of superficial abdominal locations of a pregnant mammal, the electrical signals resulting from muscular activity associated with labor;
   first memory means coupled to an output of said obtaining means for storing a digital representation of said electrical signals;
   analyzing means having an input coupled to an output of said first memory means and responsive to the stored representation therein for determining from said stored representation at least one characteristic of the labor; and
   means, responsive to said analyzing means determining said at least one characteristic of the labor, for transmitting at least a portion of said stored digital representation to a second memory means for storage in said second memory means.

21. A monitoring system as set forth in claim 20 wherein said at least one characteristic includes at least one of a uterine muscle contraction vector and an amount of dilation of the cervix.

* * * * *